United States Patent
Koyama et al.

(10) Patent No.: US 9,862,695 B2
(45) Date of Patent: *Jan. 9, 2018

(54) MONOMER HAVING N-ACYL CARBAMOYL GROUP AND LACTONE SKELETON, AND POLYMERIC COMPOUND

(71) Applicants: DAICEL CORPORATION, Osaka-shi, Osaka (JP); TOKYO OHKA KOGYO CO., LTD., Kawasaki-shi, Kanagawa (JP)

(72) Inventors: Hiroshi Koyama, Himeji (JP); Masamichi Nishimura, Himeji (JP); Naoki Yamashita, Kawasaki (JP); Yoshitaka Komuro, Kawasaki (JP); Tomoyuki Hirano, Kawasaki (JP); Yoshiyuki Utsumi, Kawasaki (JP)

(73) Assignees: DAICEL CORPORATION, Osaka-shi (JP); TOKYO OHKA KOGYO CO., LTD., Kawasaki-shi (JP)

( * ) Notice: Subject to any disclaimer, the term of this patent is extended or adjusted under 35 U.S.C. 154(b) by 211 days.

This patent is subject to a terminal disclaimer.

(21) Appl. No.: 14/835,492

(22) Filed: Aug. 25, 2015

(65) Prior Publication Data

US 2016/0060374 A1    Mar. 3, 2016

(30) Foreign Application Priority Data

Aug. 26, 2014 (JP) ................. 2014-171090

(51) Int. Cl.
| | |
|---|---|
| *G03F 7/038* | (2006.01) |
| *G03F 7/20* | (2006.01) |
| *G03F 7/32* | (2006.01) |
| *G03F 7/16* | (2006.01) |
| *C07D 307/93* | (2006.01) |

(52) U.S. Cl.
CPC ................. *C07D 307/93* (2013.01)

(58) Field of Classification Search
CPC ................................... C07D 307/93
USPC ....................................... 526/270
See application file for complete search history.

(56) References Cited

U.S. PATENT DOCUMENTS

| | | | |
|---|---|---|---|
| 9,341,947 B2 * | 5/2016 | Komuro | .......... G03F 7/30 |
| 2010/0297555 A1 | 11/2010 | Koyama et al. | |
| 2013/0130178 A1 * | 5/2013 | Iizuka | .......... C08F 12/20 |
| | | | 430/285.1 |

FOREIGN PATENT DOCUMENTS

| | | | |
|---|---|---|---|
| JP | 10-274852 A | 10/1998 | |
| JP | 2000-026446 A | 1/2000 | |
| WO | WO 2009/107327 A1 | 9/2009 | |

* cited by examiner

*Primary Examiner* — Ling Choi
*Assistant Examiner* — Chun-Cheng Wang
(74) *Attorney, Agent, or Firm* — Birch, Stewart, Kolasch & Birch, LLP

(57) ABSTRACT

Disclosed is a monomer containing an N-acylcarbamoyl group and a lactone skeleton. The monomer is exemplified by Formula (1):

[Chem. 1]

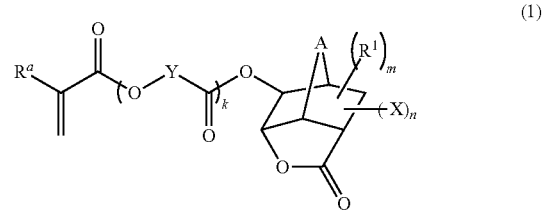

(1)

where $R^a$ is selected typically from hydrogen and $C_1$-$C_6$ alkyl; $R^1$ is, independently in each occurrence, selected typically from halogen and optionally halogenated $C_1$-$C_6$ alkyl; "A" is selected from $C_1$-$C_6$ alkylene, oxygen, sulfur, and non-bond; m represents an integer of 0 to 8; X represents, independently in each occurrence, specific N-acylcarbamoyl; n represents an integer of 1 to 9; and Y represents a $C_1$-$C_6$ divalent organic group.

20 Claims, No Drawings

MONOMER HAVING N-ACYL CARBAMOYL GROUP AND LACTONE SKELETON, AND POLYMERIC COMPOUND

JOINT RESEARCH AGREEMENT

The subject matter herein was developed as a result of a joint research agreement between Daicel Corporation and Tokyo Ohika Kogyo Co.

TECHNICAL FIELD

The present invention relates to monomers and polymeric compounds for photoresists that are used typically upon semiconductor micromachining. The present application claims priority to Japanese Patent Application No. 2014-171090 filed to Japan on Aug. 26, 2014, the entire contents of which are incorporated herein by reference.

BACKGROUND ART

Recent dramatic innovation in lithography technology for patterning in semiconductor production gives patterns with extremely fine line widths. For lithography, exposure was initially performed using i line and g line, resulting in broad line widths. This caused produced semiconductors to have low capacities. Recent technological development, however, has enabled the use of KrF excimer laser to give patterns with dramatically fine line widths. Thereafter, the development has been advanced with aiming at the application of ArF excimer laser having a still shorter wavelength, and exposure using ArF excimer laser has gone into actual use very recently. The exposure using KrF excimer laser employed conventional resins, i.e., novolac or styrenic resins. ArF excimer laser light, however, has a still shorter wavelength of 193 nm and, as having this wavelength, is absorbed by resins containing an aromatic moiety, such as the novolac and styrenic resins. To prevent this, resins for use in exposure to ArF excimer laser light have been replaced with those structurally containing no aromatic moiety, namely, replaced with alicyclic resins. Acrylic resins are mainly used as the alicyclic resins. The acrylic resins employ a mechanism in which acrylic acid is protected with a protecting group, the protected acrylic acid releases the protecting group by an acid generated upon exposure to be converted into and act as a carboxylic acid moiety, and this makes the resulting resin soluble in an alkali (alkali-soluble). Many of currently used protecting groups are alicyclic groups devoid of polar groups. The resins using these protecting groups by themselves have poor adhesion to a substrate and lack affinity typically for alkaline developers. As possible solutions to this, there is proposed a multiplicity of acrylic monomers including, as an ester moiety, a polar-group-containing alicyclic skeleton. Among them, acrylic monomers including an alicyclic skeleton containing a lactone ring as the polar group are evaluated to have high functionality and are used in great numbers. Part of such acrylic monomers can be found in Japanese Unexamined Patent Application Publication (JP-A) No. 2000-026446 (Patent Literature (PTL) 1). Monomers including an ester group of a monocyclic lactone ring are also proposed typically in Japanese Unexamined Patent Application Publication (JP-A) No. H10-274852 (PTL 2). These monomers including such a monocyclic ester group, however, lack etch resistance and seem to be not so frequently used, because the etch resistance is a function most required for resists. A technique called "immersion exposure" is currently under study. In the immersion exposure, space between a substrate and a pattern exposure system is filled with a high-density liquid. According to this technique, resist patterns are designed to be finer and finer, and with this, resist films tend to have smaller thicknesses. This induces strong demands for monomers having satisfactory etch resistance. In addition, resins containing a large amount of an alicyclic acrylic ester moiety containing a lactone ring suffer from poor solubility in organic solvents such as resist solvents. This also induces strong demands for resist-use resins having better solubility.

PCT International Publication Number WO2009/107327 (PTL 3) proposes the use of a polymer as a photoresist resin, where the polymer is prepared by polymerizing a vinyl monomer containing a ring including a cyano group and a lactone skeleton in molecule. Advantageously, this polymer is highly soluble in resist solvents and has excellent hydrolyzability. The polymer, however, is considered to be not always sufficient in affinity for alkaline developers.

CITATION LIST

Patent Literature

PTL 1: JP-A No. 2000-026446
PTL 2: JP-A No. H10-274852
PTL 3: PCT International Publication Number WO2009/107327

SUMMARY OF INVENTION

Technical Problem

The present invention has an object to provide a novel monomer that contains a lactone skeleton and is useful typically as a monomer component to form a high-performance polymer, where the high-performance polymer, when applied typically to a resist resin, offers excellent solubility in an organic solvent while maintaining stability such as chemical resistance at satisfactory level, and still has excellent solubility in an alkaline developer. The present invention has another object to provide a resin (polymer) prepared by polymerizing the monomer.

Solution to Problem

The present inventors made various investigations on monomers containing a lactone skeleton and being used to form photoresist resins. As a result, the present inventors found a compound obtained by introducing N-acylcarbamoyl into an unsaturated carboxylic acid ester containing a specific lactone-ring-containing polycyclic skeleton, where the N-acylcarbamoyl is introduced into the lactone-ring-containing polycyclic skeleton. The present inventors also found that a polymer including a monomer unit derived from the compound as a monomer component has excellent solubility in a solvent, allows an alkaline developer to extremely readily penetrate into the polymer upon development, has still better solubility in a developer because of hydrolysis of a structural moiety derived from the monomer, and, in exposed portions, is immediately dissolved in the developer; and that the compound is therefore very useful as a monomer typically for photoresist polymers. The present invention has been made based on these findings.

Specifically, the present invention provides, in an embodiment, a monomer containing an N-acylcarbamoyl group and a lactone skeleton and being represented by Formula (1):

[Chem. 1]

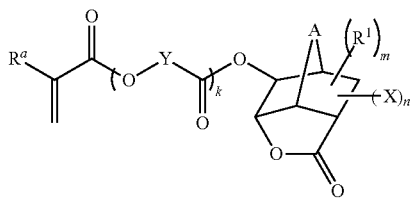

(1)

where $R^a$ is selected from hydrogen, halogen, and optionally substituted $C_1$-$C_6$ alkyl; $R^1$ is a substituent bonded to the ring and is, independently in each occurrence, selected from halogen, optionally halogenated $C_1$-$C_6$ alkyl, optionally halogenated and optionally hydroxy-protected $C_1$-$C_6$ hydroxyalkyl, carboxy which may form a salt, and substituted oxycarbonyl; "A" is selected from $C_1$-$C_6$ alkylene, oxygen, sulfur, and non-bond; m is the number of occurrence of $R^1$ and represents an integer of 0 to 8; X represents, independently in each occurrence, N-acylcarbamoyl represented by Formula (2):

[Chem. 2]

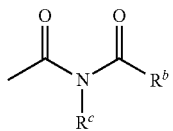

(2)

where $R^b$ and $R^c$ are each independently selected from hydrogen and an optionally substituted non-aromatic hydrocarbon group, where $R^b$ and $R^c$ may be linked to each other to form a ring with the specified nitrogen atom and carbon atom; n is the number of occurrence of X bonded to the ring and represents an integer of 1 to 9; Y represents a $C_1$-$C_6$ divalent organic group; and k is selected from 0 and 1, where $CH_2$=$C(R^a)CO$—$(O$—$Y$—$CO)_k$—$O$— group may have either of an endo conformation and an exo conformation.

The monomer may include a compound represented by Formula (1a):

[Chem. 3]

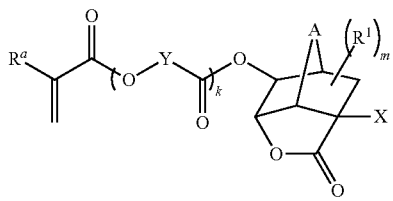

(1a)

where $R^a$ is selected from hydrogen, halogen, and optionally substituted $C_1$-$C_6$ alkyl; $R^1$ is a substituent bonded to the ring and is, independently in each occurrence, selected from halogen, optionally halogenated $C_1$-$C_6$ alkyl, optionally halogenated and optionally hydroxy-protected $C_1$-$C_6$ hydroxyalkyl, carboxy which may form a salt, and substituted oxycarbonyl; "A" is selected from $C_1$-$C_6$ alkylene, oxygen, sulfur, and non-bond; m is the number of occurrence of $R^1$ and represents an integer of 0 to 8; X represents N-acylcarbamoyl represented by Formula (2):

[Chem. 4]

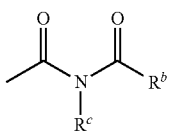

(2)

where $R^b$ and $R^c$ are each independently selected from hydrogen and an optionally substituted non-aromatic hydrocarbon group, where $R^b$ and $R^c$ may be linked to each other to form a ring with the specified nitrogen atom and carbon atom; Y represents a $C_1$-$C_6$ divalent organic group; and k is selected from 0 and 1, where $CH_2$=$C(R^a)CO$—$(O$—$Y$—$CO)_k$—$O$— group may have either of an endo conformation and an exo conformation.

The present invention also provides, in another embodiment, a polymeric compound including a monomer unit represented by Formula (I):

[Chem. 5]

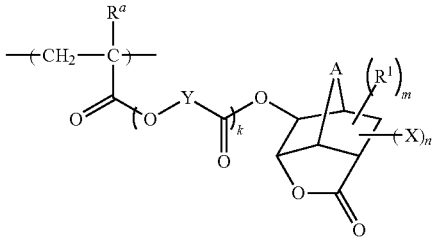

(I)

where $R^a$ is selected from hydrogen, halogen, and optionally substituted $C_1$-$C_6$ alkyl; $R^1$ is a substituent bonded to the ring and is, independently in each occurrence, selected from halogen, optionally halogenated $C_1$-$C_6$ alkyl, optionally halogenated and optionally hydroxy-protected $C_1$-$C_6$ hydroxyalkyl, carboxy which may form a salt, and substituted oxycarbonyl; "A" is selected from $C_1$-$C_6$ alkylene, oxygen, sulfur, and non-bond; m is the number of occurrence of $R^1$ and represents an integer of 0 to 8; X represents, independently in each occurrence, N-acylcarbamoyl represented by Formula (2):

[Chem. 6]

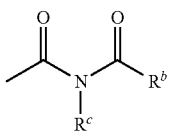

(2)

where $R^b$ and $R^c$ are each independently selected from hydrogen and an optionally substituted non-aromatic hydrocarbon group, where $R^b$ and $R^c$ may be linked to each other to form a ring with the specified nitrogen atom and carbon atom; n is the number of occurrence of X bonded to the ring and represents an integer of 1 to 9; Y represents a $C_1$-$C_6$ divalent organic group; and k is selected from 0 and 1, where $CH_2$=$C(R^a)CO$—$(O$—$Y$—$CO)_k$—$O$— group may have either of an endo conformation and an exo conformation.

The monomer unit represented by Formula (I) may include a monomer unit represented by Formula (Ia):

[Chem. 7]

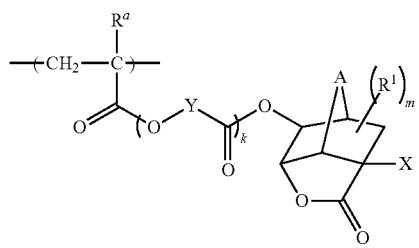

(Ia)

where $R^a$ is selected from hydrogen, halogen, and optionally substituted $C_1$-$C_6$ alkyl; $R^1$ is a substituent bonded to the ring and is, independently in each occurrence, selected from halogen, optionally halogenated $C_1$-$C_6$ alkyl, optionally halogenated and optionally hydroxy-protected $C_1$-$C_6$ hydroxyalkyl, carboxy which may form a salt, and substituted oxycarbonyl; "A" is selected from $C_1$-$C_6$ alkylene, oxygen, sulfur, and non-bond; m is the number of occurrence of $R^1$ and represents an integer of 0 to 8; X represents N-acylcarbamoyl represented by Formula (2):

[Chem. 8]

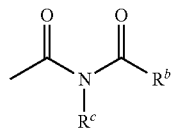

(2)

where $R^b$ and $R^c$ are each independently selected from hydrogen and an optionally substituted non-aromatic hydrocarbon group, where $R^b$ and $R^c$ may be linked to each other to form a ring with the specified nitrogen atom and carbon atom; Y represents a $C_1$-$C_6$ divalent organic group; and k is selected from 0 and 1, where $CH_2$=$C(R^a)CO$—$(O$—$Y$—$CO)_k$—$O$— group may have either of an endo conformation and an exo conformation.

The polymeric compound may further include a monomer unit capable of releasing a moiety thereof by the action of an acid to develop alkali solubility, in addition to the monomer unit represented by Formula (I).

The monomer unit capable of releasing a moiety thereof by the action of an acid to develop alkali solubility may include at least one monomer unit selected from the group consisting of monomer units represented by Formulae (Va) to (Vd):

[Chem. 9]

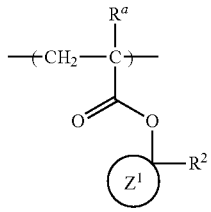

(Va)

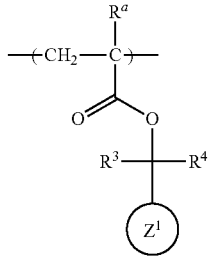

(Vb)

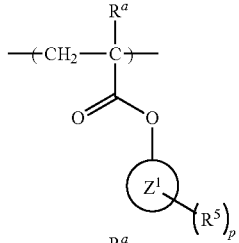

(Vc)

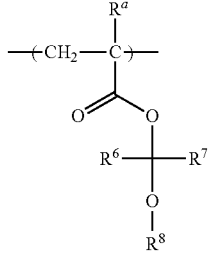

(Vd)

where Ring $Z^1$ represents an optionally substituted $C_3$-$C_{20}$ alicyclic hydrocarbon ring; $R^a$ is, independently in each occurrence, selected from hydrogen, halogen, and optionally substituted $C_1$-$C_6$ alkyl; $R^2$, $R^3$, and $R^4$ represent, identically or differently, optionally substituted $C_1$-$C_6$ alkyl; $R^5$ is a substituent bonded to Ring $Z^1$ and is, independently in each occurrence, selected from oxo, alkyl, optionally protected hydroxy, optionally protected hydroxyalkyl, and optionally protected carboxy, where at least one of occurrence(s) of $R^5$ in the number of p represents a —$COOR^d$ group, where $R^d$ is selected from an optionally substituted tertiary hydrocarbon group, tetrahydrofuranyl, tetrahydropyranyl, and oxepanyl; p represents an integer of 1 to 3; $R^6$ and $R^7$ are, identically or differently, selected from hydrogen and optionally substituted $C_1$-$C_6$ alkyl; and $R^8$ is selected from hydrogen and an organic group, where at least two of $R^6$, $R^7$, and $R^8$ may be linked to each other to form a ring with adjacent atom or atoms.

The polymeric compound may further include a monomer unit containing an alicyclic skeleton substituted with at least one substituent, in addition to the monomer unit represented by Formula (I).

The monomer unit containing an alicyclic skeleton substituted with at least one substituent may include at least one monomer unit selected from monomer units represented by Formula (VI):

[Chem. 10]

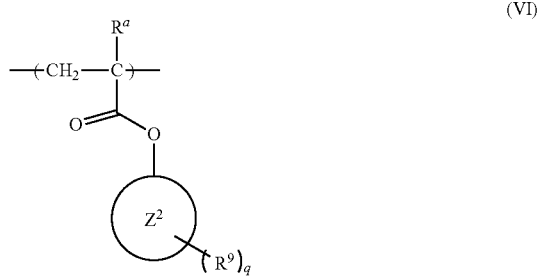

(VI)

where Ring $Z^2$ represents a $C_6$-$C_{20}$ alicyclic hydrocarbon ring; $R^a$ is selected from hydrogen, halogen, and optionally substituted $C_1$-$C_6$ alkyl; $R^9$ is a substituent bonded to Ring $Z^2$ and is, independently in each occurrence, selected from oxo, alkyl, haloalkyl, halogen, optionally protected hydroxy, optionally protected hydroxyalkyl, optionally protected mercapto, optionally protected carboxy, optionally protected amino, and optionally protected sulfo (sulfonic group); and q is the number of occurrence(s) of $R^9$ and represents an integer of 1 to 5.

The polymeric compound may include the monomer unit represented by Formula (I), the monomer unit capable of releasing a moiety thereof by the action of an acid to develop alkali solubility, and a monomer unit containing an alicyclic skeleton substituted with a substituent selected from hydroxy and hydroxymethyl.

The polymeric compound may further include a lactone-skeleton-containing monomer unit excluding the monomer unit represented by Formula (I), in addition to the monomer unit represented by Formula (I).

Locants in 6-oxabicyclo[3.2.1$^{1,5}$]octane ring and locants in 3-oxatricyclo[4.2.1.0$^{4,8}$]nonane ring are illustrated respectively in the left and right formulae:

[Chem. 11]

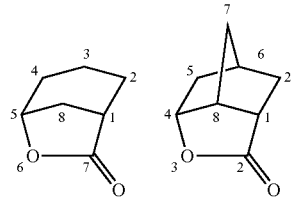

Advantageous Effects of Invention

The monomer containing an N-acylcarbamoyl group and a lactone skeleton according to the present invention may be introduced into a polymeric compound. The resulting polymeric compound has excellent solubility in an organic solvent while maintaining stability such as chemical resistance at satisfactory level. Upon development with an alkaline developer, the polymer (polymeric compound) allows the alkaline developer to readily penetrate into the polymer by the presence of N-acylcarbamoyl. This causes a structural moiety derived from the monomer to be hydrolyzed, allows the polymer to have still better solubility in the developer, and allows the polymer in exposed portions to be immediately dissolved in the developer. The polymer including the monomer unit derived from the monomer, when used as a photoresist resin, has well-balanced properties such as solvent solubility, etch resistance, and solubility in an alkaline developer upon development and enables more distinct patterning in semiconductor production.

DESCRIPTION OF EMBODIMENTS

Monomer (Compound) Containing N-Acylcarbamoyl Group and Lactone Skeleton

The monomer (compound) containing an N-acylcarbamoyl group and a lactone skeleton according to the embodiment of the present invention is exemplified by 6-oxabicyclo[3.2.1$^{1,5}$]octan-7-one derivatives and 3-oxatricyclo[4.2.1.0$^{4,}$ $_8$]nonan-2-one derivatives. The monomer (compound) is represented by Formula (1). In Formula (1), $R^a$ is selected from hydrogen, halogen, and optionally substituted $C_1$-$C_6$ alkyl; $R^1$ is a substituent bonded to the ring [e.g., 6-oxabicyclo[3.2.1$^{1,5}$]octane ring when "A" is non-bond; and 3-oxatricyclo[4.2.1.0$^{4,8}$]nonane ring when "A" is methylene] and is, independently in each occurrence, selected from halogen, optionally halogenated $C_1$-$C_6$ alkyl, optionally halogenated and optionally hydroxy-protected $C_1$-$C_6$ hydroxyalkyl, carboxy which may form a salt, and substituted oxycarbonyl; "A" is selected from $C_1$-$C_6$ alkylene, oxygen, sulfur, and non-bond; m is the number of occurrence of $R^1$ and represents an integer of 0 to 8; X represents, independently in each occurrence, N-acylcarbamoyl represented by Formula (2); n is the number of X bonded to the ring [e.g., 6-oxabicyclo[3.2.1$^{1,5}$]octane ring when "A" is non-bond; and 3-oxatricyclo[4.2.1.0$^{4,8}$]nonane ring when "A" is methylene] and represents an integer of 1 to 9; Y represents a $C_1$-$C_6$ divalent organic group; and k is selected from 0 and 1, where CH$_2$=C(R$^a$)CO—(O—Y—CO)$_k$—O— group may have either of an endo conformation and an exo conformation.

In Formula (1), X represents, independently in each occurrence, N-acylcarbamoyl represented by Formula (2). In Formula (2), $R^b$ and $R^c$ are each independently selected from hydrogen and an optionally substituted non-aromatic hydrocarbon group, where $R^b$ and $R^c$ may be linked to each other to form a ring with the specified nitrogen atom and carbon atom.

The "non-aromatic hydrocarbon group" of the "optionally substituted non-aromatic hydrocarbon group" as $R^b$ and $R^c$ is exemplified by aliphatic hydrocarbon groups, alicyclic hydrocarbon groups, and divalent groups each including two or more of them bonded to each other. The aliphatic hydrocarbon groups are exemplified by alkyl, alkenyl, and alkynyl. The alkyl is exemplified by $C_1$-$C_{20}$ alkyl such as methyl, ethyl, propyl, isopropyl, butyl, isobutyl, s-butyl, t-butyl, pentyl, hexyl, heptyl, octyl, 2-ethylhexyl, nonyl, and decyl, of which $C_1$-$C_{10}$ alkyl is preferred, and $C_1$-$C_6$ alkyl is more preferred. The alkenyl is exemplified by $C_2$-$C_{20}$ alkenyl such as vinyl, allyl, and butenyl, of which $C_2$-$C_{10}$ alkenyl is preferred, and $C_2$-$C_6$ alkenyl is more preferred. The alkynyl is exemplified by $C_2$-$C_{20}$ alkynyl such as ethynyl and propynyl, of which $C_2$-$C_{10}$ alkynyl is preferred, and $C_2$-$C_6$ alkynyl is more preferred. The alicyclic hydrocarbon groups are exemplified by 3- to 8-membered cycloalkyl such as cyclopropyl, cyclobutyl, cyclopentyl, cyclohexyl, cycloheptyl, and cyclooctyl; 3- to 8-membered cycloalkenyl such as cyclopentenyl and cyclohexenyl; and $C_4$-$C_{20}$ bridged hydrocarbon groups such as adamantyl and norbornyl, of which $C_7$-$C_{12}$ bridged hydrocarbon groups are preferred. Among them, the non-aromatic hydrocarbon group is preferably selected from $C_1$-$C_{20}$ (preferably $C_1$-$C_{10}$, and more preferably $C_1$-$C_6$) alkyl, 3- to 8-membered (preferably 5- or 6-membered) cycloalkyl, a $C_4$-$C_{20}$ (preferably $C_7$-$C_{12}$) bridged hydrocarbon group, and a group including two or more of them bonded to each other.

The "substituent(s)" of the "optionally substituted non-aromatic hydrocarbon group" (non-aromatic hydrocarbon group which may have one or more substituents) is exemplified by halogen such as fluorine; hydroxy; alkoxy such as methoxy, of which $C_1$-$C_6$ alkoxy is typified; carboxy; alkoxycarbonyl such as methoxycarbonyl, of which $C_1$-$C_6$ alkoxy-carbonyl is typified; acyl such as acetyl, of which $C_1$-$C_6$ acyl is typified; cyano; aryl such as phenyl, of which $C_6$-$C_{14}$ aryl is typified; alkyl such as methyl, of which $C_1$-$C_{20}$ alkyl is typified, $C_1$-$C_{10}$ alkyl is preferred, and $C_1$-$C_6$ alkyl is more preferred; alkenyl such as vinyl, of which $C_2$-$C_6$ alkenyl is typified; cycloalkyl such as cyclohexyl, of which $C_3$-$C_{12}$ cycloalkyl is typified; and nitro.

$R^b$ and $R^c$ may be linked to each other to form a ring with the specified nitrogen atom and carbon atom. The ring is exemplified by 4- to 12-membered (preferably 5- or 6-membered) non-aromatic nitrogen-containing heterocyclic rings such as β-lactam ring (a 4-membered ring), γ-lactam ring (a 5-membered ring), and δ-lactam ring (a 6-membered ring). One or more substituents may be bonded to atoms constituting the ring. Such substituents are exemplified by groups as with the "substituent(s)" of the "optionally substituted non-aromatic hydrocarbon group" as $R^b$ and $R^c$. Among them, preferred is $C_1$-$C_{20}$ alkyl such as methyl, ethyl, propyl, isopropyl, butyl, isobutyl, s-butyl, t-butyl, pentyl, hexyl, heptyl, octyl, 2-ethylhexyl, nonyl, and decyl, of which $C_1$-$C_{10}$ alkyl is more preferred, and $C_1$-$C_6$ alkyl is furthermore preferred. Of these substituents, $C_1$-$C_6$ alkyl such as methyl is preferred.

$R^b$ and $R^c$ are each preferably selected from hydrogen, $C_1$-$C_6$ (in particular $C_1$-$C_4$) alkyl, 3- to 8-membered (in particular 5- or 6-membered) cycloalkyl, and $C_4$-$C_{20}$ (in particular $C_7$-$C_{12}$) bridged hydrocarbon groups. It is also preferred that $R^b$ and $R^c$ are linked to each other to form a 5- or 6-membered non-aromatic nitrogen-containing heterocyclic ring with the specified nitrogen atom and carbon atom. From the viewpoint of affinity for an alkaline developer, $R^c$ is preferably hydrogen so as to constitute an acidic functional group. In particular, in a preferred combination of $R^b$ and $R^c$, $R^c$ is hydrogen; and $R^b$ is selected from $C_1$-$C_6$ (in particular $C_1$-$C_4$) alkyl, 3- to 8-membered (in particular 5- or 6-membered) cycloalkyl, and a $C_4$-$C_{20}$ (in particular $C_7$-$C_{12}$) bridged hydrocarbon group.

The halogen as $R^a$ and $R^1$ in Formula (1) is exemplified by fluorine, chlorine, and bromine. The $C_1$-$C_6$ alkyl is exemplified by methyl, ethyl, propyl, isopropyl, butyl, isobutyl, s-butyl, t-butyl, pentyl, and hexyl. Among them, $C_1$-$C_4$ alkyl is preferred, and methyl is particularly preferred. The halogenated $C_1$-$C_6$ alkyl is exemplified by chloroalkyl such as chloromethyl; and fluoroalkyl such as trifluoromethyl, 2,2,2-trifluoroethyl, and pentafluoroethyl, of which $C_1$-$C_3$ fluoroalkyl is preferred. The substituted $C_1$-$C_6$ alkyl as $R^a$ is exemplified by the halogenated $C_1$-$C_6$ alkyl.

As $R^1$, the $C_1$-$C_6$ hydroxyalkyl is exemplified by hydroxymethyl, 2-hydroxyethyl, 1-hydroxyethyl, 3-hydroxypropyl, 2-hydroxypropyl, 4-hydroxybutyl, and 6-hydroxyhexyl. The halogenated $C_1$-$C_6$ hydroxyalkyl is exemplified by difluorohydroxymethyl, 1,1-difluoro-2-hydroxyethyl, 2,2-difluoro-2-hydroxyethyl, and 1,1,2,2-tetrafluoro-2-hydroxyethyl. Of such optionally halogenated $C_1$-$C_6$ hydroxyalkyl, preferred is $C_1$ or $C_2$ (particularly $C_1$) hydroxyalkyl or hydroxyhaloalkyl. The hydroxy-protecting group in the optionally halogenated $C_1$-$C_6$ hydroxyalkyl is exemplified by protecting groups generally used as hydroxy-protecting groups in the area of organic syntheses, such as methyl, methoxymethyl, and other groups that form an ether or acetal bond with the oxygen atom constituting the hydroxy group; and acetyl, benzoyl, and other groups that form an ester bond with the oxygen atom constituting the hydroxy group. The salt of carboxy is exemplified by alkali metal salts, alkaline earth metal salts, and transition metal salts.

The substituted oxycarbonyl is exemplified by alkoxycarbonyl such as methoxycarbonyl, ethoxycarbonyl, isopropyloxycarbonyl, and propoxycarbonyl, of which ($C_1$-$C_4$ alkoxy)-carbonyl is typified; alkenyloxycarbonyl such as vinyloxycarbonyl and allyloxycarbonyl, of which ($C_2$-$C_4$ alkoxy)-carbonyl is typified; cycloalkyloxycarbonyl such as cyclohexyloxycarbonyl; and aryloxycarbonyl such as phenyloxycarbonyl.

$R^a$ is preferably selected from hydrogen; $C_1$-$C_3$ alkyl such as methyl; and $C_1$-$C_3$ haloalkyl such as trifluoromethyl. In particular, $R^a$ is preferably selected from hydrogen and methyl. $R^1$ is preferably selected typically from $C_1$-$C_3$ alkyl or haloalkyl (e.g., methyl or trifluoromethyl); optionally hydroxy-protected $C_1$-$C_3$ hydroxyalkyl or hydroxyhaloalkyl (in particular, optionally protected hydroxymethyl such as hydroxymethyl or acetoxymethyl); and substituted oxycarbonyl.

The number m is 0 to 8, preferably 0 to 6, and more preferably 0 to 3. $R^1$, when present in two or more occurrences, may be identical to or different from each other. The number n is 1 to 9, preferably 1 to 5, and more preferably 1 or 2. X, when present in two or more occurrences, may be identical to or different from each other. When "A" is non-bond, the substituent(s) X may be bonded at any of the 1-position, 2-position, 3-position, 4-position, 5-position, and 8-position of the 6-oxabicyclo[3.2.1$^{1,5}$]octane ring, but is preferably bonded at the 1-position (α-position of the lactone) or 2-position, and is particularly preferably bonded at the 1-position (α-position of the lactone). When "A" is selected from $C_1$-$C_6$ alkylene, oxygen, and sulfur, the substituent(s) X may be bonded at any position such as the 1-position, 4-position, 5-position, 6-position, 7-position, 8-position, and 9-position typically of the 3-oxatricyclo[4.2.1.0$^{4,8}$]nonane ring, but is preferably bonded at the 1-position or 9-position of the 3-oxatricyclo[4.2.1.0$^{4,8}$] nonane ring (or any of positions corresponding to these positions) and is particularly preferably bonded at the 1-position (or a position corresponding to this; α-position of the lactone).

"A" is selected from $C_1$-$C_6$ alkylene, oxygen, sulfur, and non-bond. The $C_1$-$C_6$ alkylene is exemplified by methylene, ethylene, and propylene, each of which may be substituted with alkyl. In particular, "A" is preferably selected from $C_1$-$C_6$ alkylene and non-bond.

Y represents a $C_1$-$C_6$ divalent organic group. The $C_1$-$C_6$ divalent organic group is exemplified by $C_1$-$C_6$ alkylene such as methylene, ethylene, propylene, and butylene; $C_2$-$C_6$ alkenylene such as vinylene; cycloalkenylene such as cyclopentylene and cyclohexylene; and divalent organic groups each including two or more of them bonded to each other through a linkage group, where the linkage group is exemplified by ether bond (—O—), thioether bond (—S—), and ester bond (—COO—; —OCO—). In particular, Y is preferably selected typically from methylene, ethylene, and propylene. Groups corresponding to the exemplified groups, except for being halogenated, in particular, except for being fluorinated, are also useful herein.

The monomer represented by Formula (1) and containing an N-acylcarbamoyl group and a lactone skeleton is representatively exemplified by 1-substituted (X)-6-oxabicyclo[3.2.1$^{1,5}$]octan-7-one compounds (including stereoisomers), 2-substituted (X)-6-oxabicyclo[3.2.1$^{1,5}$]octan-7-one compounds (including stereoisomers), 1-substituted (X)-5-(meth)acryloyloxy-3-oxatricyclo[4.2.1.0$^{4,8}$]nonan-2-one compounds (including stereoisomers), and 9-substituted (X)-5-(meth)acryloyloxy-3-oxatricyclo[4.2.1.0$^{4,8}$]nonan-2-one compounds (including stereoisomers), which are represented by formulae below; and compounds of Formula (1) corresponding to them, in which "A" is selected from alkylene excluding methylene, oxygen, and sulfur. In the formulae, R represents a CH$_2$=C(R$^a$)CO—(O—Y—CO)$_k$— group; Ac represents acetyl; and X as a substituent represents N-acylcarbamoyl represented by Formula (2).

[Chem. 12]

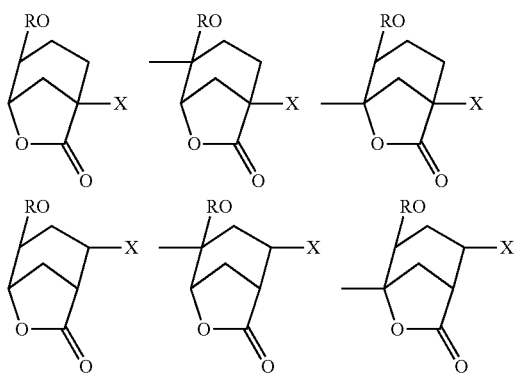

[Chem. 13]

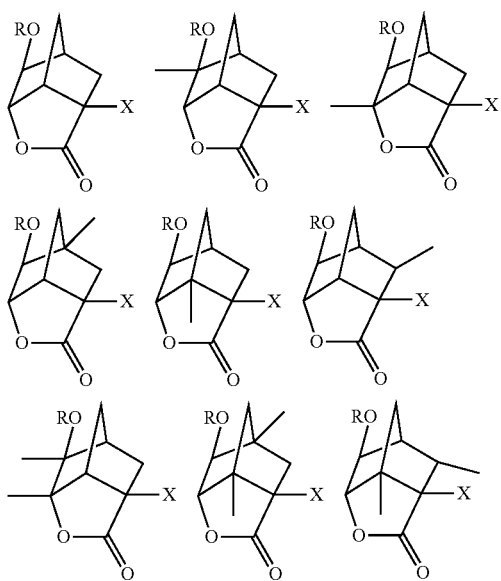

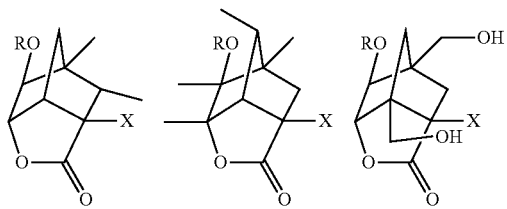

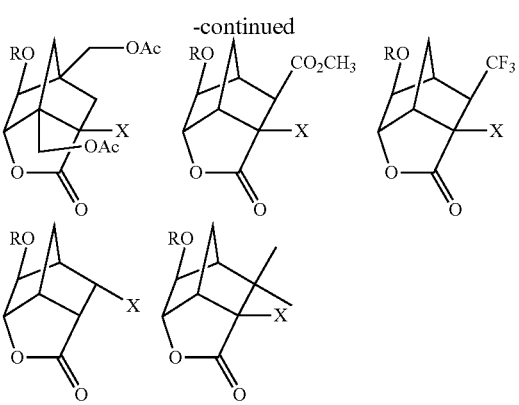

Preferred examples of the monomer represented by Formula (1) and containing an N-acylcarbamoyl group and a lactone skeleton include a compound represented by Formula (1a). The compound represented by Formula (1a) corresponds to the monomer represented by Formula (1) and containing an N-acylcarbamoyl group and a lactone skeleton, in which N-acylcarbamoyl X is bonded at the α-position of the lactone.

The monomer (compound) represented by Formula (1) and containing an N-acylcarbamoyl group and a lactone skeleton may be produced typically by any of methods (i) to (iii) as follows.

In the method (i), a compound represented by Formula (3) and containing cyano and a lactone skeleton is allowed to react with an acid anhydride represented by Formula (7) in the presence of an acid, followed by hydrolysis, where Formulae (3) and (7) are expressed as follows:

[Chem. 14]

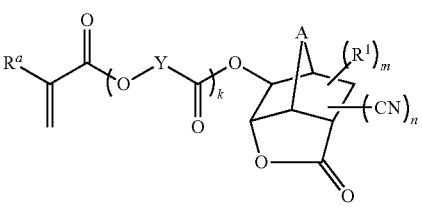

(3)

where R$^a$, R$^1$, A, Y, k, and m are as defined above; and n is the number of cyano group(s) bonded to the ring and represents an integer of 1 to 9, where CH$_2$=C(R$^a$)CO—(O—Y—CO)$_k$—O— group may have either of an endo conformation and an exo conformation, $$(R^b—CO)_2O \qquad (7)$$

where R$^b$ is as defined above. This method gives a compound of Formula (1) in which X is —CO—NH—COR$^b$.

The compound represented by Formula (3) can be produced typically by the method described in PCT International Publication Number WO2009/107327 (PTL 3).

The acid is exemplified by Lewis acids such as tin tetrachloride (SnCl$_4$), aluminum chloride (AlCl$_3$), titanium tetrachloride (TiCl$_4$), silicon tetrachloride (SiCl$_4$), and boron trifluoride ether complexes. The acid may be used in an amount of typically about 0.1 to about 10 moles, preferably about 1 to about 5 moles, and more preferably about 1 to about 2 moles, per mole of the compound represented by Formula (3).

The acid anhydride represented by Formula (7) is representatively exemplified by aliphatic carboxylic anhydrides such as acetic anhydride, propionic anhydride, and butyric anhydride; alicyclic carboxylic anhydrides such as bis(cyclopentanecarboxylic acid)anhydride and bis(cyclohexanecarboxylic acid) anhydride; and bridged carboxylic anhydrides such as bis(adamantanecarboxylic acid)anhydrides and bis(norbornanecarboxylic acid)anhydrides. The acid anhydride represented by Formula (7) may be used in an amount of typically about 1 to about 100 moles, and preferably about 2 to about 50 moles, per mole of the compound represented by Formula (3).

The reaction between the compound represented by Formula (3) and the acid anhydride represented by Formula (7) may be performed at a reaction temperature of typically 0° C. to 200° C., and preferably 50° C. to 150° C.

The hydrolysis is preferably performed in the presence of an acid catalyst. The acid catalyst is exemplified by inorganic acids such as hydrochloric acid, sulfuric acid, and polyphosphoric acids; and sulfonic acids such as p-toluenesulfonic acid and methanesulfonic acid. The hydrolysis may be performed at a temperature of typically −10° C. to 100° C., and preferably 0° C. to 50° C.

The formed compound represented by Formula (1) can be purified typically by subjecting the reaction mixture to a separation procedure such as filtration, concentration, extraction, pH adjustment, crystallization, recrystallization, or column chromatography, or any combination of them.

In the method (ii), the compound represented by Formula (3) is hydrolyzed to give a compound containing a carbamoyl and a lactone skeleton and being represented by Formula (4a):

[Chem. 15]

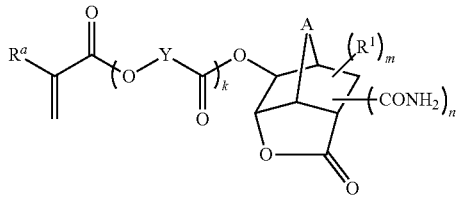

(4a)

where $R^a$, $R^1$, A, Y, k, and m are as defined above; and n is the number of carbamoyl (—CONH$_2$) bonded to the ring and represents an integer of 1 to 9, where CH$_2$=C($R^a$)CO—(O—Y—CO)$_k$—O— group may have either of an endo conformation and an exo conformation. This compound is allowed to react with an acyl halide represented by Formula (8):

$R^b$—COZ (8)

where $R^b$ is as defined above; and Z represents halogen. This method gives a compound of Formula (1) in which X is —CO—NH—COR$^b$.

The halogen as Z is exemplified by chlorine, bromine, and iodine.

The hydrolysis of the compound represented by Formula (3) may be performed typically in the presence of an acid catalyst. The acid catalyst is exemplified by inorganic acids such as hydrochloric acid, sulfuric acid, and polyphosphoric acid; and sulfonic acids such as p-toluenesulfonic acid and methanesulfonic acid. The hydrolysis may be performed at a temperature of typically −10° C. to 100° C., and preferably 0° C. to 50° C.

The compound represented by Formula (4a) as formed by the reaction can be purified typically by subjecting the reaction mixture to a separation procedure such as filtration, concentration, extraction, pH adjustment, crystallization, recrystallization, or column chromatography, or any combination of them.

The acyl halide represented by Formula (8) is representatively exemplified by aliphatic carboxylic acid halides such as acetyl chloride, acetyl bromide, propionyl chloride, and propionyl bromide; cycloalkanecarboxylic acid halides such as cyclopentanecarbonyl chloride and cyclohexanecarbonyl chloride; and bridged carboxylic acid halides such as adamantanecarbonyl chloride and norbornanecarbonyl chloride.

The reaction between the compound represented by Formula (4a) and the acyl halide represented by Formula (8) is preferably performed in the presence of a base. The base is exemplified by tertiary amines such as triethylamine; and heteroaromatic nitrogen-containing compounds such as pyridine. The acyl halide represented by Formula (8) may be used in an amount of typically about 1 to about 5 moles, and preferably about 1.2 to about 3 moles, per mole of the compound represented by Formula (4a). The base may be used in an amount of typically about 1 to about 5 moles, and preferably about 1.5 to about 5 moles, per mole of the compound represented by Formula (4a). The reaction may be performed at a temperature of typically about −10° C. to about 100° C., and preferably about 0° C. to about 60° C. After the reaction, the reaction mixture may be subjected to treatment with an acid such as dilute hydrochloric acid as needed.

The formed compound represented by Formula (1) can be purified typically by subjecting the reaction mixture to a separation procedure such as filtration, concentration, extraction, pH adjustment, crystallization, recrystallization, or column chromatography, or any combination of them.

In the method (iii), the compound represented by Formula (3) is allowed to react with an alcohol represented by Formula (9) in the presence of an acid (e.g., sulfuric acid), where Formula (9) is expressed as follows:

$R^c$OH (9)

where $R^c$ is as defined above, except hydrogen. This gives a compound containing N-alkyl-substituted carbamoyl and a lactone skeleton and being represented by Formula (4b):

[Chem. 16]

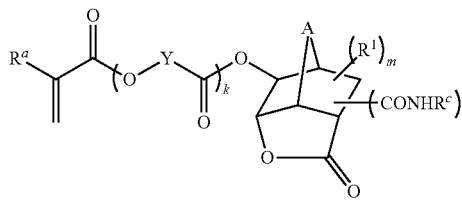

(4b)

where $R^a$, $R^1$, A, Y, k, and m are as defined above; $R^c$ is as defined above, except hydrogen; n is the number of the group (—CONHR$^c$) bonded to the ring and represents an integer of 1 to 9, where CH$_2$=C($R^a$)CO—(O—Y—CO)$_k$—O— group may have either of an endo conformation and an exo conformation. This compound is allowed to react with the acyl halide represented by Formula (8). The method can give a compound of Formula (1) in which X is —CO—NR$^c$—COR$^b$.

The acid (e.g., sulfuric acid) may be used in an amount of typically about 0.1 to about 2 moles, and preferably about 1 to about 1.5 moles, per mole of the compound represented by Formula (3). The alcohol represented by Formula (9) may be used in an amount of typically about 1 to about 5 moles, and preferably about 1.2 to about 3 moles, per mole of the compound represented by Formula (3).

The formed compound represented by Formula (4b) and containing N-alkyl-substituted carbamoyl and a lactone skeleton can be purified typically by subjecting the reaction mixture to a separation procedure such as filtration, concentration, extraction, pH adjustment, crystallization, recrystallization, or column chromatography, or any combination of them.

The reaction between the compound represented by Formula (4b) and the acyl halide represented by Formula (8) is preferably performed in the presence of a base. The base is exemplified by tertiary amines such as triethylamine; and heteroaromatic nitrogen-containing compounds such as pyridine. The acyl halide represented by Formula (8) may be used in an amount of typically about 1 to about 5 moles, and preferably about 1.2 to about 3 moles, per mole of the compound represented by Formula (4b). The base may be used in an amount of typically about 1 to about 5 moles, and preferably about 1.5 to about 5 moles, per mole of the compound represented by Formula (4b). The reaction may be performed at a temperature of typically about −10° C. to about 100° C., and preferably about 0° C. to about 60° C.

The formed compound represented by Formula (1) can be purified typically by subjecting the reaction mixture to a separation procedure such as filtration, concentration, extraction, pH adjustment, crystallization, recrystallization, or column chromatography, or any combination of them.

Polymeric Compound

The polymeric compound according to the embodiment of the present invention includes a monomer unit (constitutional repeating unit) corresponding to (derived from) the monomer represented by Formula (1) and containing an N-acylcarbamoyl group and a lactone skeleton. Namely, the polymeric compound includes the monomer unit represented by Formula (I). The polymeric compound may include each of different monomer units alone or in combination as the monomer unit of Formula (I). The polymeric compound as above may be prepared by subjecting the monomer represented by Formula (1) and containing an N-acylcarbamoyl group and a lactone skeleton to polymerization.

The monomer unit represented by Formula (I) includes a specific skeleton such as an 6-oxabicyclo[3.2.1$^{3,5}$]octan-7-one skeleton bonded with the N-acylcarbamoyl represented by Formula (2), or an 3-oxatricyclo[4.2.1.0$^{4,8}$]nonan-2-one skeleton bonded with the N-acylcarbamoyl represented by Formula (2). The monomer unit has a higher affinity for water and/or an alkaline developer, as compared with a unit including a cyano-substituted 6-oxabicyclo[3.2.1$^{1,5}$]octan-7-one skeleton and a unit including a cyano-substituted 3-oxatricyclo[4.2.1.0$^{4,8}$]nonan-2-one skeleton. The polymeric compound according to the embodiment of the present invention is therefore useful as high-functional polymers that are used in areas requiring affinity for water and/or an alkaline developer. In particular, the polymeric compound is useful as photoresist resins (resins for photoresists).

The polymeric compound according to the embodiment of the present invention may further include one or more other monomer units according to the intended use and required functions, in addition to the monomer unit represented by Formula (I). Such an other monomer unit may be formed by copolymerizing a polymerizable unsaturated monomer corresponding to the other monomer unit with the monomer represented by Formula (1) and containing an N-acylcarbamoyl group and a lactone skeleton.

The other monomer unit is exemplified by monomer units capable of releasing a moiety thereof by the action of an acid to develop alkali solubility (monomer units that convert the polymer into an alkali-soluble one). These monomer units are exemplified by monomer units exemplified by Formulae (Va), (Vb), (Vc), and (Vd). Polymerizable unsaturated monomers corresponding to the monomer units represented by Formulae (Va), (Vb), (Vc), and (Vd) are respectively represented by Formula (5a), (5b), (5c), and (5d):

[Chem. 17]

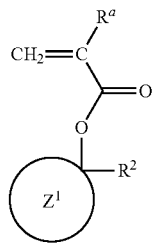

(5a)

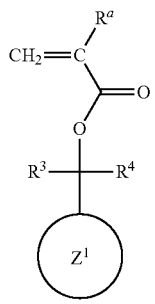

(5b)

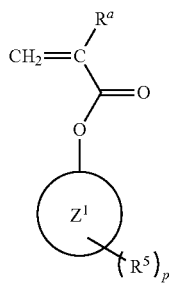

(5c)

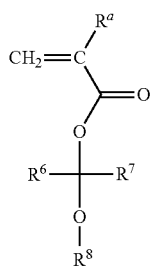

(5d)

In the formulae, Ring $Z^1$ represents, independently in each occurrence, an optionally substituted $C_3$-$C_{20}$ alicyclic hydrocarbon ring; $R^a$ is as defined above; $R^2$, $R^3$, and $R^4$ represent, identically or differently, optionally substituted $C_1$-$C_6$ alkyl; $R^5$ is a substituent bonded to Ring $Z^1$ and is, independently in each occurrence, selected from oxo, alkyl, optionally protected hydroxy, optionally protected hydroxyalkyl, and optionally protected carboxy, where at least one of occurrence(s) of $R^5$ in the number of p represents a —COOR$^d$ group, where $R^d$ is selected from an optionally substituted tertiary hydrocarbon group, tetrahydrofuranyl, tetrahydropyranyl, and oxepanyl; p represents an integer of 1 to 3; $R^6$ and $R^7$ are, identically or differently, selected from hydrogen and optionally substituted $C_1$-$C_6$ alkyl; and $R^8$ is selected from hydrogen and an organic group, where at least two of $R^6$, $R^7$, and $R^8$ may be linked to each other to form a ring with adjacent atom or atoms.

In Formulae (5a) to (5c), the $C_3$-$C_{20}$ alicyclic hydrocarbon ring as Ring $Z^1$ may be a monocyclic ring or a polycyclic ring such as a fused ring or a bridged ring. The alicyclic hydrocarbon ring is representatively exemplified by cyclopropane, cyclobutane, cyclopentane, cyclohexane, cyclooctane, cyclodecane, adamantane, norbornane, norbornene, bornane, isobornane, perhydroindene, decahydronaphthalene, perhydrofluorene (tricyclo[7.4.0.0$^{3,8}$]tridecane), perhydroanthracene, tricyclo[5.2.1.0$^{2,6}$]decane, tricyclo[4.2.2.1$^{2,5}$]undecane, and tetracyclo[4.4.0.1$^{2,5}$.1$^{7,10}$] dodecane rings. The alicyclic hydrocarbon ring may be substituted with one or more substituents. The substituents are exemplified by alkyl such as methyl, of which $C_1$-$C_4$ alkyl is typified; halogen such as chlorine; optionally protected hydroxy; oxo; and optionally protected carboxy. Ring $Z^1$ is preferably a polycyclic alicyclic hydrocarbon ring (bridged hydrocarbon ring) such as adamantane ring.

The optionally substituted $C_1$-$C_6$ alkyl as $R^2$, $R^3$, $R^4$, $R^6$, and $R^7$ in Formulae (5a), (5b), and (5d) is exemplified by straight or branched chain $C_1$-$C_6$ alkyl such as methyl, ethyl, propyl, isopropyl, butyl, isobutyl, s-butyl, t-butyl, and hexyl; and $C_1$-$C_6$ haloalkyl such as trifluoromethyl. The alkyl as $R^5$ in Formula (5c) is exemplified by alkyl containing 1 to about 20 carbon atoms, such as methyl, ethyl, propyl, isopropyl, butyl, isobutyl, s-butyl, t-butyl, hexyl, octyl, decyl, and dodecyl. As $R^5$, the optionally protected hydroxy is exemplified by hydroxy; and substituted oxy including $C_1$-$C_4$ alkoxy such as methoxy, ethoxy, and propoxy. The optionally protected hydroxyalkyl is exemplified by groups each including the optionally protected hydroxy bonded through $C_1$-$C_6$ alkylene. The optionally protected carboxy is exemplified by a —COOR$^f$ group, where $R^f$ is selected from hydrogen and alkyl. The alkyl herein is exemplified by straight or branched chain $C_1$-$C_6$ alkyl such as methyl, ethyl, propyl, isopropyl, butyl, isobutyl, s-butyl, t-butyl, and hexyl. In $R^5$, the tertiary hydrocarbon group as $R^d$ of the —COOR$^d$ group is exemplified by t-butyl, t-amyl, 2-methyl-2-adamantyl, and (1-methyl-1-adamantyl)ethyl. The tetrahydrofuranyl is exemplified by 2-tetrahydrofuranyl; the tetrahydropyranyl is exemplified by 2-tetrahydropyranyl; and the oxepanyl is exemplified by 2-oxepanyl.

The organic group as $R^8$ is exemplified by groups each containing at least one group selected from hydrocarbon groups and heterocyclic groups. The hydrocarbon groups include aliphatic hydrocarbon groups, alicyclic hydrocarbon groups, aromatic hydrocarbon groups, and groups each including two or more of them bonded to each other. The aliphatic hydrocarbon groups are exemplified by straight or branched chain alkyl such as methyl, ethyl, propyl, isopropyl, butyl, isobutyl, s-butyl, t-butyl, hexyl, and octyl, of which $C_1$-$C_8$ alkyl is typified; straight or branched chain alkenyl such as allyl, of which $C_2$-$C_8$ alkenyl is typified; and straight or branched chain alkynyl such as propynyl, of which $C_2$-$C_8$ alkynyl is typified. The alicyclic hydrocarbon groups are exemplified by cycloalkyl such as cyclopropyl, cyclopentyl, and cyclohexyl, of which 3- to 8-membered cycloalkyl is typified; cycloalkenyl such as cyclopentenyl and cyclohexenyl, of which 3- to 8-membered cycloalkenyl is typified; and bridged carbocyclic groups such as adamantyl and norbornyl, of which $C_4$-$C_{20}$ bridged carbocyclic groups are typified. The aromatic hydrocarbon groups are exemplified by $C_6$-$C_{14}$ aromatic hydrocarbon groups such as phenyl and naphthyl. The groups each including an aliphatic hydrocarbon group and an aromatic hydrocarbon group bonded to each other are exemplified by benzyl and 2-phenylethyl. Each of these hydrocarbon groups may be substituted with one or more substituents. The substituents are exemplified by alkyl (e.g., $C_1$-$C_4$ haloalkyl (e.g., $C_1$-$C_4$ haloalkyl), halogen, optionally protected hydroxy, optionally protected hydroxymethyl, optionally protected carboxy, and oxo. The protecting groups herein can be selected from protecting groups commonly used in the area of organic syntheses.

The heterocyclic groups are exemplified by heterocyclic groups each including at least one heteroatom selected from oxygen, sulfur, and nitrogen.

Preferred exemplary organic groups are organic groups each containing $C_1$-$C_8$ alkyl and/or a cyclic skeleton. The "ring" constituting the cyclic skeleton includes monocyclic or polycyclic non-aromatic or aromatic carbocyclic or heterocyclic rings. In particular, preferred are monocyclic or polycyclic non-aromatic carbocyclic rings and lactone rings (to which a non-aromatic carbocyclic ring may be fused). The monocyclic non-aromatic carbocyclic rings are exemplified by cycloalkane rings each containing 3 to about 15 members, such as cyclopentane and cyclohexane rings.

The polycyclic non-aromatic carbocyclic rings (bridged carbocyclic rings) are exemplified by adamantane ring; norbornane ring and norbornene-containing rings such as norbornane, norbornene, bornane, isobornane, tricyclo[5.2.1.0$^{2,6}$]decane, and tetracyclo[4.4.0.1$^{2,5}$.1$^{7,10}$]dodecane rings; rings corresponding to polycyclic aromatic fused rings, except for being hydrogenated, such as perhydroindene, decahydronaphthalene (perhydronaphthalene), perhydrofluorene (tricyclo[7.4.0.0$^{3,8}$]tridecane), and perhydroanthracene rings, of which fully hydrogenated rings are preferred; bicyclic, tricyclic, tetracyclic, and other bridged carbocyclic rings such as tricyclo[4.2.2.1$^{2,5}$]undecane ring, of which bridged carbocyclic rings each containing about 6 to about 20 carbon atoms are typified. The lactone rings are exemplified by γ-butyrolactone, 4-oxatricyclo[4.3.1.1$^{3,8}$]undecan-5-one, 4-oxatricyclo[4.2.1.0$^{3,7}$]nonan-5-one, and 4-oxatricyclo[5.2.1.0$^{2,6}$]decan-5-one rings.

The ring constituting the cyclic skeleton may be substituted with one or more substituents. The substituents are exemplified by alkyl such as methyl, of which $C_1$-$C_4$ alkyl is typified; haloalkyl such as trifluoromethyl, of which $C_1$-$C_4$ haloalkyl is typified; halogen such as chlorine and fluorine; optionally protected hydroxy; optionally protected hydroxyalkyl; optionally protected mercapto; optionally protected carboxy; optionally protected amino; and optionally protected sulfo. The protecting groups herein can be selected from protecting groups commonly used in the area of organic syntheses.

The ring constituting the cyclic skeleton may be bonded directly, or indirectly through a linkage group, to the specified oxygen atom (oxygen atom at the adjacent position to $R^8$) in Formula (5d). The linkage group is exemplified by straight or branched chain alkylene such as methylene, methylmethylene, dimethylmethylene, ethylene, propylene, and trimethylene; carbonyl; oxygen (ether bond; —O—); oxycarbonyl (ester bond; —COO—); aminocarbonyl (amido bond; —CONH—); and groups each including two or more of them linked to each other.

At least two of $R^6$, $R^7$, and $R^8$ may be linked to each other to form a ring with adjacent atom or atoms. The ring is exemplified by cycloalkane rings such as cyclopropane, cyclopentane, and cyclohexane rings; oxygen-containing rings such as tetrahydrofuran, tetrahydropyran, and oxepane rings; and bridged rings.

The compounds represented by Formulae (5a) to (5d) may individually include stereoisomers. Each of different stereoisomers may be used alone or in combination.

The compounds represented by Formula (5a) are representatively exemplified by, but not limited to, 2-(meth)acryloyloxy-2-methyladamantane, 1-hydroxy-2-(meth)acryloyloxy-2-methyladamantane, 5-hydroxy-2-(meth)acryloyloxy-2-methyladamantane, and 2-(meth)acryloyloxy-2-ethyladamantane.

The compounds represented by Formula (5b) are representatively exemplified by, but not limited to, 1-(1-(meth)acryloyloxy-1-methylethyl)adamantane, 1-hydroxy-3-(1-(meth)acryloyloxy-1-methylethyl)adamantane, 1-(1-ethyl-1-(meth)acryloyloxypropyl)adamantane, and 1-(1-(meth)acryloyloxy-1-methylpropyl)adamantane.

The compounds represented by Formula (5c) are representatively exemplified by, but not limited to, 1-t-butoxycarbonyl-3-(meth)acryloyloxyadamantane and 1-(2-tetrahydropyranyloxycarbonyl)-3-(meth)acryloyloxyadamantane.

The compounds represented by Formula (5d) are representatively exemplified by, but not limited to, 1-adamantyloxy-1-ethyl(meth)acrylate, 1-adamantylmethyloxy-1-ethyl(meth)acrylate, 2-(1-adamantylethyl)oxy-1-ethyl(meth)acrylate, 1-bornyloxy-1-ethyl(meth)acrylate, 2-norbornyloxy-1-ethyl(meth)acrylate, 2-tetrahydropyranyl(meth)acrylate, and 2-tetrahydrofuranyl(meth)acrylate.

The compound represented by Formula (5d) may be prepared typically by allowing a corresponding vinyl ether compound to react with (meth)acrylic acid by a common method using an acid catalyst. Typically, 1-adamantyloxy-1-ethyl(meth)acrylate may be prepared by allowing 1-adamantyl vinyl ether to react with (meth)acrylic acid in the presence of an acid catalyst.

In addition to the above monomers, the other monomer units are further exemplified by monomer units that can impart to the polymeric compound one or more properties such as hydrophilicity and water solubility, or can allow the polymeric compound to have higher or better properties. Monomers corresponding to such monomer units are exemplified by polar-group-containing monomers such as hydroxy-containing monomers (including hydroxy-protected compounds), mercapto-containing monomers (including mercapto-protected compounds), carboxy-containing monomers (including carboxy-protected compounds), amino-containing monomers (including amino-protected compounds), sulfo-containing monomers (including sulfo-protected compounds), lactone-skeleton-containing monomers, cyclic-ketone-skeleton-containing monomers, acid-anhydride-containing monomers, imido-containing monomers, and other monomers.

Such other monomer units are exemplified by monomer units containing an alicyclic skeleton substituted with at least one substituent, such as monomer units represented by Formula (VI). Polymerizable unsaturated monomers corresponding to the monomer units represented by Formula (VI) are represented by Formula (6):

[Chem. 18]

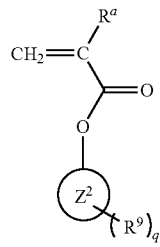

In Formula (6), Ring $Z^2$ represents a $C_6$-$C_{20}$ alicyclic hydrocarbon ring; $R^a$ is as defined above; $R^9$ is a substituent bonded to Ring $Z^2$ and is, independently in each occurrence, selected from oxo, alkyl, haloalkyl, halogen, optionally protected hydroxy, optionally protected hydroxyalkyl, optionally protected mercapto, optionally protected carboxy, optionally protected amino, and optionally protected sulfo; and q is the number of occurrence(s) of $R^9$ and represents an integer of 1 to 5.

Of the monomers of Formula (6), some monomers correspond to the polar-group-containing monomers that can impart to the polymeric compound hydrophilicity and/or water solubility or can allow the polymeric compound to have better hydrophilicity and/or better water solubility. These monomers are monomers of Formula (6) in which at least one of occurrence(s) of $R^9$ in the number of q is selected from oxo, optionally protected hydroxy, optionally protected hydroxyalkyl, optionally protected mercapto, optionally protected carboxy, optionally protected amino, and optionally protected sulfo.

The $C_6$-$C_{20}$ alicyclic hydrocarbon ring as Ring $Z^2$ may be a monocyclic ring, or a polycyclic ring such as a bridged ring. The alicyclic hydrocarbon ring is representatively exemplified by cyclohexane, cyclooctane, cyclodecane, adamantane, norbornane, norbornene, bornane, isobornane, perhydroindene, decahydronaphthalene, perhydrofluorene (tricyclo[7.4.0.0$^{3,8}$]tridecane), perhydroanthracene, tricyclo[5.2.1.0$^{2,6}$]decane, tricyclo[4.2.2.1$^{2,5}$]undecane, and tetracyclo[4.4.0.1$^{2,5}$.1$^{7,10}$]dodecane rings. Of the alicyclic hydrocarbon rings, particularly preferred are bridged alicyclic hydrocarbon rings such as adamantane ring.

As $R^9$ in Formula (6), the alkyl is exemplified by straight or branched chain alkyl containing 1 to about 20 carbon atoms, such as methyl, ethyl, propyl, isopropyl, butyl, isobutyl, s-butyl, t-butyl, hexyl, octyl, decyl, and dodecyl, of which $C_1$-$C_4$ alkyl is preferred. The haloalkyl is exemplified by haloalkyl containing 1 to about 20 carbon atoms, such as trifluoromethyl, of which $C_1$-$C_4$ haloalkyl is preferred. The halogen is exemplified by fluorine and chlorine. The optionally protected amino is exemplified by amino; and substituted amino including $C_1$-$C_4$ alkyl-amino such as methylamino, ethylamino, and propylamino. The optionally protected sulfo is exemplified by a —SO$_3$R$^g$ group, where R$^g$ is selected from hydrogen and alkyl. The alkyl herein is exemplified by straight or branched chain $C_1$-$C_6$ alkyl such as methyl, ethyl, propyl, isopropyl, butyl, isobutyl, s-butyl, t-butyl, and hexyl. The optionally protected hydroxy, optionally protected hydroxyalkyl, optionally protected mercapto, and optionally protected carboxy as $R^9$ are as exemplified above.

The compounds represented by Formula (6) are representatively exemplified by, but not limited to, 1-hydroxy-3-(meth)acryloyloxyadamantane, 1,3-dihydroxy-5-(meth)

acryloyloxyadamantane, 1-carboxy-3-(meth)acryloyloxyadamantane, 1,3-dicarboxy-5-(meth)acryloyloxyadamantane, 1-carboxy-3-hydroxy-5-(meth)acryloyloxyadamantane, 1-t-butoxycarbonyl-3-(meth)acryloyloxyadamantane, 1,3-bis(t-butoxycarbonyl)-5-(meth)acryloyloxyadamantane, 1-t-butoxycarbonyl-3-hydroxy-5-(meth)acryloyloxyadamantane, 1-(2-tetrahydropyranyloxycarbonyl)-3-(meth)acryloyloxyadamantane, 1,3-bis(2-tetrahydropyranyloxycarbonyl)-5-(meth)acryloyloxyadamantane, 1-hydroxy-3-(2-tetrahydropyranyloxycarbonyl)-5-(meth)acryloyloxyadamantane, and 1-(meth)acryloyloxy-4-oxoadamantane.

Of the monomers corresponding to the monomer units containing an alicyclic skeleton substituted with at least one substituent, preferred are monomers each containing an alicyclic skeleton substituted with at least one substituent selected from hydroxy and hydroxymethyl. The alicyclic skeleton is exemplified by adamantane skeleton.

The other monomer units are further exemplified by lactone-skeleton-containing monomer units excluding the monomer units represented by Formula (I). Specifically, examples of polymerizable unsaturated monomers [lactone-ring-containing monomers (excluding the compounds represented by Formula (1))] corresponding to the lactone-skeleton-containing monomer units [excluding the monomer units represented by Formula (I)] are as follows.

The examples are: 1-(meth)acryloyloxy-4-oxatricyclo[4.3.1.1$^{3,8}$]undecan-5-one, 1-(meth)acryloyloxy-4,7-dioxatricyclo[4.4.1.11$^{3,9}$]dodecane-5,8-dione, 1-(meth)acryloyloxy-4,8-dioxatricyclo[4.4.1.1$^{3,9}$]dodecane-5,7-dione, 1-(meth)acryloyloxy-5,7-dioxatricyclo[4.4.1.1$^{3,9}$]dodecane-4,8-dione, 2-(meth)acryloyloxy-4-oxatricyclo[4.2.1.0$^{3,7}$]nonan-5-one, 2-(meth)acryloyloxy-2-methyl-4-oxatricyclo[4.2.1.0$^{3,7}$]nonan-5-one, 2-(meth)acryloyloxy-6-methyl-4-oxatricyclo[4.2.1.0$^{3,7}$]nonan-5-one, 2-(meth)acryloyloxy-9-methyl-4-oxatricyclo[4.2.1.0$^{3,7}$]nonan-5-one, 2-(meth)acryloyloxy-9-carboxy-4-oxatricyclo[4.2.1.0$^{3,7}$]nonan-5-one, 2-(meth)acryloyloxy-9-methoxycarbonyl-4-oxatricyclo[4.2.1.0$^{3,7}$]nonan-5-one, 2-(meth)acryloyloxy-9-ethoxycarbonyl-4-oxatricyclo[4.2.1.0$^{3,7}$]nonan-5-one, 2-(meth)acryloyloxy-9-t-butoxycarbonyl-4-oxatricyclo[4.2.1.0$^{3,7}$]nonan-5-one, 8-(meth)acryloyloxy-4-oxatricyclo[5.2.1.0$^{2,6}$]decan-5-one, 9-(meth)acryloyloxy-4-oxatricyclo[5.2.1.0$^{2,6}$]decan-5-one, 4-(meth)acryloyloxy-6-oxabicyclo[3.2.1]octan-7-one, 4-(meth)acryloyloxy-4-methyl-6-oxabicyclo[3.2.1]octan-7-one, 4-(meth)acryloyloxy-5-methyl-6-oxabicyclo[3.2.1]octan-7-one, 4-(meth)acryloyloxy-4,5-dimethyl-6-oxabicyclo[3.2.1]octan-7-one, 6-(meth)acryloyloxy-2-oxabicyclo[2.2.2]octane-3-one, 6-(meth)acryloyloxy-6-methyl-2-oxabicyclo[2.2.2]octane-3-one, 6-(meth)acryloyloxy-1-methyl-2-oxabicyclo[2.2.2]octane-3-one, 6-(meth)acryloyloxy-1,6-dimethyl-2-oxabicyclo[2.2.2]octane-3-one, β-(meth)acryloyloxy-γ-butyrolactone, β-(meth)acryloyloxy-α,α-dimethyl-γ-butyrolactone, β-(meth)acryloyloxy-γ,γ-dimethyl-γ-butyrolactone, β-(meth)acryloyloxy-α,α,β-trimethyl-γ-butyrolactone, β-(meth)acryloyloxy-β,γ,γ-trimethyl-γ-butyrolactone, β-(meth)acryloyloxy-α,α,β,γ,γ-pentamethyl-γ-butyrolactone, α-(meth)acryloyloxy-γ-butyrolactone, α-(meth)acryloyloxy-α-methyl-γ-butyrolactone, α-(meth)acryloyloxy-β,β-dimethyl-γ-butyrolactone, α-(meth)acryloyloxy-α,β,β-trimethyl-γ-butyrolactone, α-(meth)acryloyloxy-γ,γ-dimethyl-γ-butyrolactone, α-(meth)acryloyloxy-α,γ,γ-trimethyl-γ-butyrolactone, α-(meth)acryloyloxy-β,β,γ,γ-tetramethyl-γ-butyrolactone, α-(meth)acryloyloxy-α,β,β,γ,γ-pentamethyl-γ-butyrolactone, and γ-(meth)acryloyloxy-γ,γ-dimethyl-γ-butyrolactone.

The polymeric compound according to the embodiment of the present invention may contain the monomer unit represented by Formula (I) in a proportion not critical, but generally about 1 to about 90 mole percent, preferably about 5 to about 80 mole percent, and more preferably about 10 to about 60 mole percent, based on the total amount of all monomer units constituting the polymeric compound. The polymeric compound may contain the monomer unit capable of releasing a moiety thereof by the action of an acid to develop alkali solubility in a proportion of typically about 10 to about 95 mole percent, preferably about 15 to about 90 mole percent, and more preferably about 20 to about 60 mole percent. The polymeric compound may contain a monomer unit corresponding to at least one monomer selected from hydroxy-containing monomers, mercapto-containing monomers and carboxy-containing monomers in a proportion of typically about 0 to about 60 mole percent, preferably about 5 to about 50 mole percent, and more preferably about 10 to about 40 mole percent. The monomer unit just mentioned above is exemplified by monomer units represented by Formula (VI) in which at least one of the occurrence(s) of $R^9$ in the number of q is selected from optionally protected hydroxy, optionally protected hydroxyalkyl, optionally protected mercapto, and optionally protected carboxy.

Polymerization of a monomer mixture to form the polymeric compound according to the embodiment of the present invention may be performed by a common process for use in the production typically of acrylic polymers, such as solution polymerization, bulk polymerization, suspension polymerization, bulk-suspension polymerization, or emulsion polymerization. In particular, solution polymerization is preferred. Of such solution polymerization processes, dropping polymerization is more preferred. Specifically, the dropping polymerization may be performed by a technique such as a technique (i), (ii), or (iii) as follows. In the technique (i), a monomer solution is prepared by dissolving monomers in an organic solvent. Separately, a polymerization initiator solution is prepared by dissolving a polymerization initiator in an organic solvent. The prepared monomer solution and polymerization initiator solution are independently added dropwise to the organic solvent held at a constant temperature (given temperature). In the technique (ii), a mixture solution is prepared by dissolving monomers and a polymerization initiator in an organic solvent. The mixture solution is added dropwise to the organic solvent held at a constant temperature. In the technique (iii), a monomer solution is prepared by dissolving monomers in an organic solvent. Separately, a polymerization initiator solution is prepared by dissolving a polymerization initiator in an organic solvent. The polymerization initiator solution is added dropwise to the monomer solution held at a constant temperature.

The polymerization solvent for use herein may be selected from known solvents which are exemplified by ethers including chain ethers such as diethyl ether and glycol ethers (e.g., propylene glycol monomethyl ether), and cyclic ethers such as tetrahydrofuran and dioxane; esters such as methyl acetate, ethyl acetate, butyl acetate, ethyl lactate, and glycol ether esters (e.g., propylene glycol monomethyl ether acetate); ketones such as acetone, methyl ethyl ketone, methyl isobutyl ketone, and cyclohexanone; amides such as N,N-dimethylacetamide and N,N-dimethylformamide; sulfoxides such as dimethyl sulfoxide; alcohols such as methanol, ethanol, and propanol; hydrocarbons including aromatic hydrocarbons such as benzene, toluene, and xylenes, aliphatic hydrocarbons such as hexane, and alicyclic hydrocarbons such as cyclohexane; and mixture of these solvents. The polymerization initiator for use herein may be selected from known polymerization initiators. The polymerization may be performed at a temperature that is selectable as appropriate within the range typically of about 30° C. to about 150° C.

The polymeric compound (polymer) obtained by the polymerization may be purified by precipitation or reprecipitation. A solvent for use in precipitation or reprecipitation may be either of an organic solvent and water, and may be a solvent mixture. The organic solvent for use as the precipitation or reprecipitation solvent is exemplified by hydrocarbons including aliphatic hydrocarbons such as pentane, hexane, heptane, and octane, alicyclic hydrocarbons such as cyclohexane and methylcyclohexane, and aromatic hydrocarbons such as benzene, toluene, and xylenes; halogenated hydrocarbons including halogenated aliphatic hydrocarbons such as methylene chloride, chloroform, and carbon tetrachloride, and halogenated aromatic hydrocarbons such as chlorobenzene and dichlorobenzene; nitro compounds such as nitromethane and nitroethane; nitriles such as acetonitrile and benzonitrile; ethers including chain ethers such as diethyl ether, diisopropyl ether, and dimethoxyethane, and cyclic ethers such as tetrahydrofuran and dioxane; ketones such as acetone, methyl ethyl ketone, and diisobutyl ketone; esters including aliphatic carboxylic acid esters such as ethyl acetate and butyl acetate; carbonates such as dimethyl carbonate, diethyl carbonate, ethylene carbonate, and propylene carbonate; alcohols such as methanol, ethanol, propanol, isopropyl alcohol, and butanol; carboxylic acids such as acetic acid; and solvent mixtures including any of these solvents.

Among them, preferred as the organic solvent for use as the precipitation or reprecipitation solvent are a solvent containing at least a hydrocarbon (in particular, an aliphatic hydrocarbon such as hexane); and a solvent mixture of methanol and water. The solvent containing at least a hydrocarbon may have a ratio (weight ratio, at 25° C.) of the hydrocarbon to another solvent of typically about 10:90 to about 99:1, preferably about 30:70 to about 98:2, and more preferably about 50:50 to about 97:3. The hydrocarbon is exemplified by aliphatic hydrocarbons such as hexane; and the other solvent is exemplified by aliphatic carboxylic acid esters such as ethyl acetate.

The polymeric compound may have a weight-average molecular weight (Mw) of typically about 1000 to about 500000 and preferably about 3000 to about 50000, and a molecular weight distribution (Mw/Mn) of typically about 1.5 to about 2.5. The symbol Mn refers to a number-average molecular weight. The molecular weights Mn and Mw are each values as calibrated with a polystyrene standard.

The polymeric compound according to the embodiment of the present invention has stability such as chemical resistance at satisfactory levels, has excellent solubility in an organic solvent, and still offers excellent affinity for water and/or an alkaline developer. In addition, after the hydrolysis of the lactone ring typically as a result of development with an alkaline developer, the polymeric compound offers excellent solubility in water and/or the alkaline developer. The polymeric compound is therefore usable as high-functional polymers in a variety of areas.

The present invention also relates to a photoresist composition that includes the polymeric compound according to the embodiment of the present invention and a photoacid generator. The photoresist composition may generally further include a resist solvent. The photoresist composition can be prepared typically by adding the photoacid generator to a solution of the polymeric compound according to the embodiment of the present invention (a solution in the resist solvent).

The photoacid generator is exemplified by common or known compounds that efficiently generate an acid upon exposure (light irradiation). The compounds are exemplified by diazonium salts; iodonium salts such as diphenyliodonium hexafluorophosphate; sulfonium salts such as triphenylsulfonium hexafluoroantimonate, triphenylsulfonium hexafluorophosphate, and triphenylsulfonium methanesulfonate; sulfonic acid esters such as 1-phenyl-1-(4-methylphenyl)sulfonyloxy-1-benzoylmethane, 1,2,3-trisulfonyloxymethylbenzene, 1,3-dinitro-2-(4-phenylsulfonyloxymethyl)benzene, and 1-phenyl-1-(4-methylphenylsulfonyloxymethyl)-1-hydroxy-1-benzoylmethane; oxathiazole derivatives; s-triazine derivatives; disulfone derivatives such as diphenyl disulfone; imide compounds; oxime sulfonates; diazonaphthoquinone; and benzoin tosylate. Each of different photoacid generator may be used alone or in combination.

The photoacid generator may be used in an amount as selected within the range of typically about 0.1 to about 30 parts by weight, preferably about 1 to about 25 parts by weight, and more preferably about 2 to about 20 parts by weight, per 100 parts by weight of the polymeric compound, whereas the amount can be selected as appropriate according typically to the strength of the acid generated upon light irradiation (exposure) and to proportions of constitutional repeating units in the polymeric compound (photoresist resin).

The resist solvent is exemplified by the glycol solvents, ester solvents, and ketone solvents exemplified as the polymerization solvent; and mixtures of these solvents. Among them, preferred are propylene glycol monomethyl ether, propylene glycol monomethyl ether acetate, ethyl lactate, methyl isobutyl ketone, methyl amyl ketone, and mixtures of them. Among them, particularly preferred are solvents containing propylene glycol monomethyl ether acetate, such as single solvent of propylene glycol monomethyl ether acetate; a solvent mixture of propylene glycol monomethyl ether acetate and propylene glycol monomethyl ether; and a solvent mixture of propylene glycol monomethyl ether acetate and ethyl lactate.

The photoresist composition may contain the polymeric compound in a concentration of typically about 10 to about 40 percent by weight. The photoresist composition may further include one or more of other components such as alkali-soluble components and colorants. The alkali-soluble components are exemplified by alkali-soluble resins such as novolac resins, phenolic resins, imide resins, and carboxy-containing resins. The colorants are exemplified by dyestuffs.

The photoresist composition which may be prepared in the above manner is applied onto a base material or substrate and dried to give a coated film (resist film). The film is exposed to light through a predetermined mask (or further subjected to post-exposure baking) to form a latent-image pattern, followed by development to form a highly precise fine pattern.

The base material or substrate is exemplified by silicon wafers, metals, plastics, glass, and ceramics. The application of the photoresist composition may be performed using a common coating device such as spin coaters, dip coaters, and roll coaters. The coated film may have a thickness of typically about 0.1 to about 20 μm, and preferably about 0.3 to about 2 μm The exposure may be performed using light of a variety of wavelengths, such as ultraviolet rays and X rays. For semiconductor resist use, the exposure may be performed generally using any of g line, i line, and excimer laser (e.g., XeCl, KrF, KrCl, ArF, and ArCl laser) light. The exposure may be performed at an energy of typically about 1 to about 1000 mJ/cm$^2$, and preferably about 10 to about 500 mJ/cm$^2$.

The light irradiation (exposure) allows the photoacid generator to generate an acid. Assume that the polymeric compound is used for photoresist and contains a constitutional repeating unit capable of releasing a moiety thereof by the action of an acid to develop alkali solubility (constitutional repeating unit containing an acid-leaving group). The acid causes the protecting group (leaving group) typically of a carboxy group in the constitutional repeating unit to leave immediately, and this gives, for example, an unprotected carboxy group that contributes to alkali solubility. Accordingly, the polymeric compound contributes to the precise formation of a predetermined pattern by development with water or an alkaline developer.

EXAMPLES

The present invention will be illustrated in further detail with reference to several examples below. It should be noted, however, that the examples are by no means intended to limit the scope of the present invention. The weight-average molecular weights (Mw) and number-average molecular weights (Mn) of polymeric compounds are as determined by gel permeation chromatographic (GPC) assay using a refractometer (RI) with tetrahydrofuran as a solvent and calibrated with a polystyrene standard. The gel permeation chromatographic assay was performed using three "KF-806L" columns (Showa Denko K.K.) connected in series at a column temperature of 40° C., a refractometer temperature of 40° C., and a tetrahydrofuran flow rate of 0.8 ml/min.

Example 1

There was prepared 1-(N-acetylcarbamoyl)-5-methacryloyloxy-3-oxatricyclo[4.2.1.0$^{4,8}$]nonan-2-one according to the reaction formula:

[Chem. 19]

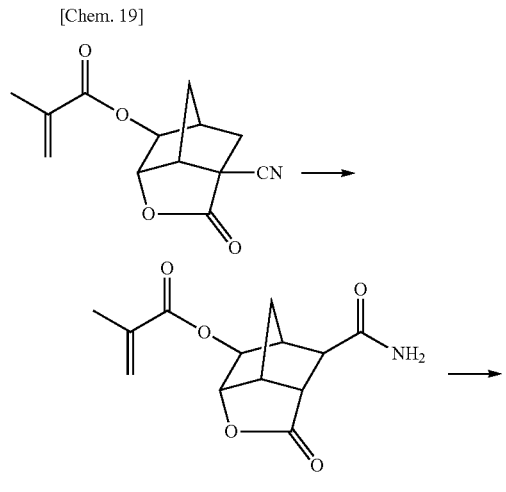

-continued

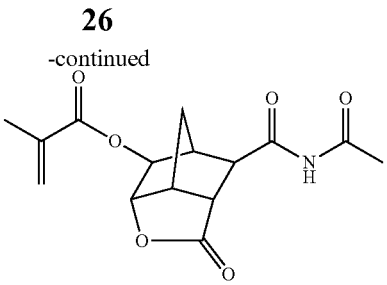

In a nitrogen-purged, 100-ml three-neck flask equipped with a stirrer, were placed 5 g (20.2 mmol) of 1-cyano-5-methacryloyloxy-3-oxatricyclo[4.2.1.0$^{4,8}$]nonan-2-one and 10.5 g of concentrated hydrochloric acid, followed by mixing with stirring. The stirring was performed for 46 hours while maintaining the liquid temperature at 15° C. to 25° C. on a water bath. The resulting mixture was cooled on an ice bath and combined with 90 g of water added dropwise over 30 minutes while maintaining the internal temperature at 0° C. to 5° C. Precipitated crystals were filtrated, rinsed with 5 g of water two times, and yielded crude crystals. The crude crystals were subjected to silica gel column chromatography and yielded 1.7 g (6.4 mmol) of 1-carbamoyl-5-methacryloyloxy-3-oxatricyclo[4.2.1.0$^{4,8}$]nonan-2-one in a yield of 32%. The NMR spectral data of this compound were as follows:

$^1$H-NMR (DMSO-d$^6$) δ: 7.58 (1H, brs), 7.37 (1H, brs), 6.07 (1H, s), 5.72 (1H, s), 4.65 (1H, d), 4.56 (1H, s), 3.48 (1H, d), 2.51-2.54 (1H, m), 2.44 (1H, dd), 1.92 (1H, d), 1.89 (3H, s), 1.76 (1H, dd), 1.59 (1H, d)

In a nitrogen-purged, 100-ml three-neck flask equipped with a stirrer, were placed 2.2 g (8.2 mmol) of 1-carbamoyl-5-methacryloyloxy-3-oxatricyclo[4.2.1.0$^{4,8}$]nonan-2-one synthetically prepared by the above method, 14.2 g of acetonitrile, and 2.22 g (21.9 mmol) of triethylamine, followed by mixing with stirring. The mixture was combined with 1.5 g (19.1 mmol) of acetyl chloride added dropwise while maintaining the liquid temperature at 0° C. to 10° C. on an ice bath, followed by stirring at 45° C. for 9 hours. The reaction mixture was combined with 43.4 g of ethyl acetate and then combined with 10.9 g of 2.3 percent by weight hydrochloric acid while maintaining the internal temperature at 0° C. to 10° C. on an ice bath. An organic phase was separated, washed sequentially with 21.7 g of 8 percent by weight sodium bicarbonate water and with 21.7 g of water, and the resulting organic phase was concentrated in a vacuum at 35° C. The concentrated residue was subjected to silica gel column chromatography (hexane:ethyl acetate=3: 1) and yielded 0.05 g (0.16 mmol) of 1-(N-acetylcarbamoyl)-5-methacryloyloxy-3-oxatricyclo[4.2.1.0$^{4,8}$]nonan-2-one in a yield of 2%. The NMR spectral data of this compound are as follows:

$^1$H-NMR (CDCl$_3$) δ: 9.72 (1H, brs), 6.12 (1H, m), 5.64 (1H, m), 4.67 (1H, m), 4.65 (1H, m), 3.49 (1H, m), 2.70 (1H, m), 2.42 (3H, s), 2.29-2.33 (1H, m), 2.09-2.15 (3H, m), 1.95 (3H, s)

Example 2

There was prepared 1-(N-acetylcarbamoyl)-5-(2-methacryloyloxyacetoxy)-3-oxatricyclo[4.2.1.0$^{4,8}$]nonan-2-one according to the reaction formula:

[Chem. 20]

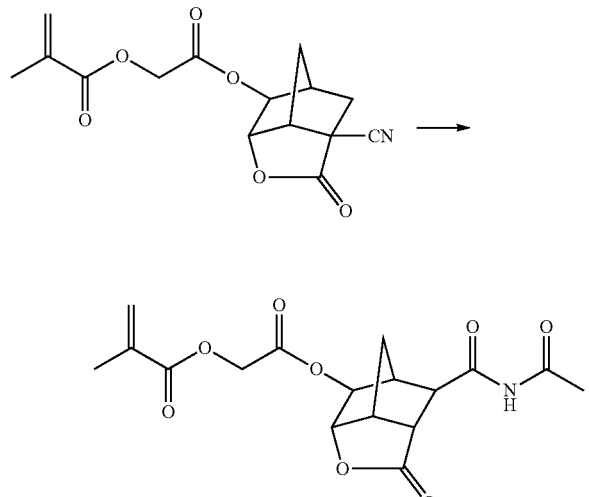

In a nitrogen-purged, 200-ml three-neck flask equipped with a stirrer, were placed 3.0 g (9.8 mmol) of 1-cyano-5-(2-methacryloyloxyacetoxy)-3-oxatricyclo[4.2.1.0$^{4,8}$]nonan-2-one and 10.0 g (98 mmol) of acetic anhydride, followed by mixing with stirring. The mixture was combined with 3.3 g of (12.8 mmol) of tin(IV) chloride while maintaining the liquid temperature at 25° C. or lower on a water bath, followed by stirring at a liquid temperature of 80° C. for 6 hours. After the completion of the reaction, the reaction mixture was cooled on an ice bath, combined with 100 g of ethyl acetate and 130 g of 5 N hydrochloric acid, and stirred for 30 minutes while maintaining the internal temperature at 25° C. or lower. An organic phase was separated, further combined with 200 g of ethyl acetate and 300 g of 5 N hydrochloric acid, and stirred for 30 minutes. The resulting organic phase was separated and concentrated in a vacuum to give a crude product. The crude product was subjected to silica gel column chromatography and yielded 0.51 g (1.4 mmol) of 1-(N-acetylcarbamoyl)-5-(2-methacryloyloxyacetoxy)-3-oxatricyclo[4.2.1.0$^{4,8}$]nonan-2-one in a yield of 14%. The NMR spectral data of this compound are as follows:

$^1$H-NMR (CDCl$_3$) δ: 9.68 (1H, brs), 6.23 (1H, m), 5.69 (1H, m), 4.62-4.70 (4H, m), 3.48 (1H, m), 2.69 (1H, m), 2.42 (3H, s), 2.28-2.32 (1H, m), 2.05-2.15 (3H, m), 1.99 (3H, s)

Example 3

Synthesis of Polymeric Compound (Copolymer) Having Structure:

[Chem. 21]

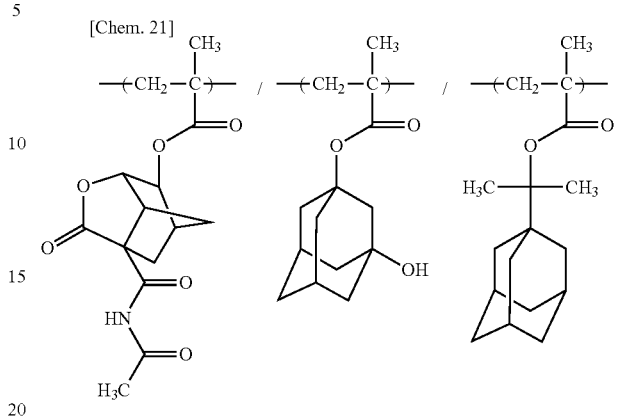

In a nitrogen atmosphere, 59.5 g of cyclohexanone were placed in a round-bottomed flask equipped with a reflux condenser, a stirring bar, and a three-way stopcock and, while maintaining the temperature at 80° C. with stirring, combined with a monomer solution added dropwise at a constant rate over 6 hours. The monomer solution was a mixture of 13.41 g (43.7 mmol) of 1-(N-acetylcarbamoyl)-5-methacryloyloxy-3-oxatricyclo[4.2.1.0$^{4,8}$]nonan-2-one, 5.15 g (21.8 mmol) of 1-hydroxy-3-methacryloyloxyadamantane, 11.44 g (43.7 mmol) of 1-(1-methacryloyloxy-1-methylethyl)adamantane, 1.80 g of dimethyl 2,2'-azobisisobutyrate [trade name V-601, Wako Pure Chemical Industries, Ltd.], and 110.5 g of cyclohexanone. After the completion of the dropwise addition, the resulting mixture was continuously stirred for further 2 hours. After the completion of the polymerization reaction, the reaction mixture was added dropwise to a stirred 9:1 (weight ratio) mixture of hexane and ethyl acetate in an amount of 7 times the amount of the reaction mixture. The resulting precipitates were separated by filtration, dried under reduced pressure, and yielded 27.5 g of the desired polymeric compound. The polymeric compound as recovered was analyzed by GPC and found to have a weight-average molecular weight (Mw) of 8600 and a molecular weight distribution (Mw/Mn) of 1.87.

Example 4

Synthesis of Polymeric Compound (Copolymer) Having Structure:

[Chem. 22]

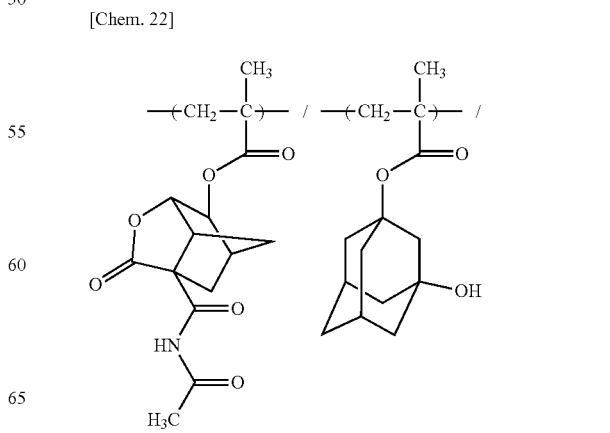

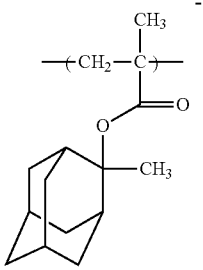

The procedure of Example 3 was performed, except for using, as monomer components, 13.98 g (45.5 mmol) of 1-(N-acetylcarbamoyl)-5-methacryloyloxy-3-oxatricyclo[4.2.1.0$^{4,8}$]nonan-2-one, 5.37 g (22.8 mmol) of 1-hydroxy-3-methacryloyloxyadamantane, and 10.65 g (45.5 mmol) of 2-methacryloyloxy-2-methyladamantane, and yielded 24.6 g of the desired polymeric compound. The polymeric compound as recovered was analyzed by GPC and found to have a weight-average molecular weight (Mw) of 9100 and a molecular weight distribution (Mw/Mn) of 1.92.

Example 5

Synthesis of Polymeric Compound (Copolymer) Having Structure:

[Chem. 23]

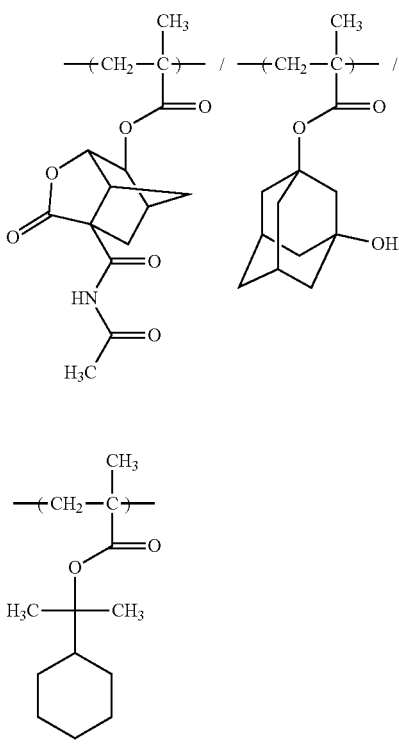

The procedure of Example 3 was performed, except for using, as monomer components, 14.50 g (47.2 mmol) of 1-(N-acetylcarbamoyl)-5-methacryloyloxy-3-oxatricyclo[4.2.1.0$^{4,8}$]nonan-2-one, 5.57 g (23.6 mmol) of 1-hydroxy-3-methacryloyloxyadamantane, and 9.92 g (47.2 mmol) of 1-(1-methacryloyloxy-1-methylethyl)cyclohexane, and yielded 27.8 g of the desired polymeric compound. The polymeric compound as recovered was analyzed by GPC and found to have a weight-average molecular weight (Mw) of 8500 and a molecular weight distribution (Mw/Mn) of 1.85.

Example 6

Synthesis of Polymeric Compound (Copolymer) Having Structure:

[Chem. 24]

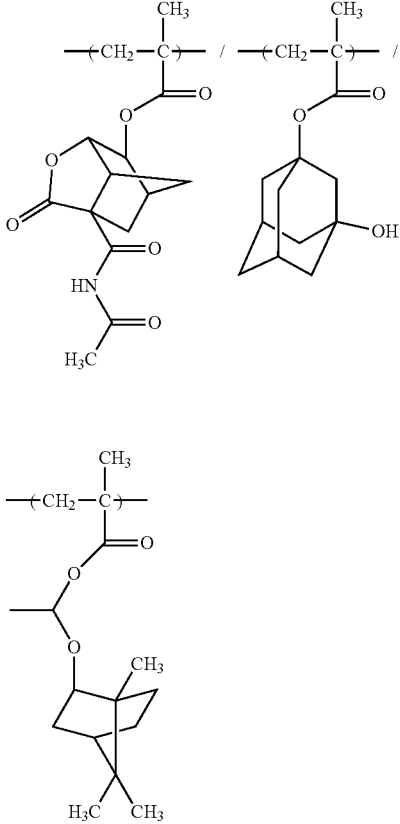

The procedure of Example 3 was performed, except for using, as monomer components, 13.33 g (43.4 mmol) of 1-(N-acetylcarbamoyl)-5-methacryloyloxy-3-oxatricyclo[4.2.1.0$^{4,8}$]nonan-2-one, 5.12 g (21.7 mmol) of 1-hydroxy-3-methacryloyloxyadamantane, and 11.55 g (43.4 mmol) of 1-(bornyloxy)ethyl methacrylate, and yielded 27.3 g of the desired polymeric compound. The polymeric compound as recovered was analyzed by GPC and found to have a weight-average molecular weight (Mw) of 8500 and a molecular weight distribution (Mw/Mn) of 1.86.

Example 7

Synthesis of Polymeric Compound (Copolymer) Having Structure:

[Chem. 25]

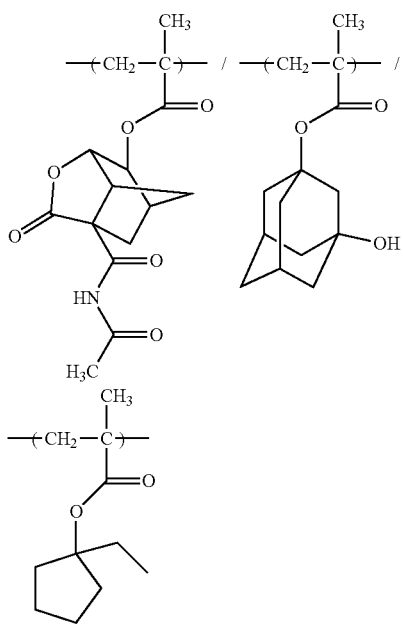

The procedure of Example 3 was performed, except for using, as monomer components, 15.17 g (49.4 mmol) of 1-(N-acetylcarbamoyl)-5-methacryloyloxy-3-oxatricyclo[4.2.1.0$^{4,8}$]nonan-2-one, 5.83 g (24.7 mmol) of 1-hydroxy-5-methacryloyloxyadamantane, and 9.00 g (49.4 mmol) of 1-methacryloyloxy-1-ethylcyclopentane, and yielded 26.8 g of the desired polymeric compound. The polymeric compound as recovered was analyzed by GPC and found to have a weight-average molecular weight (Mw) of 8700 and a molecular weight distribution (Mw/Mn) of 1.88.

Example 8

Synthesis of Polymeric Compound (Copolymer) Having Structure:

[Chem. 26]

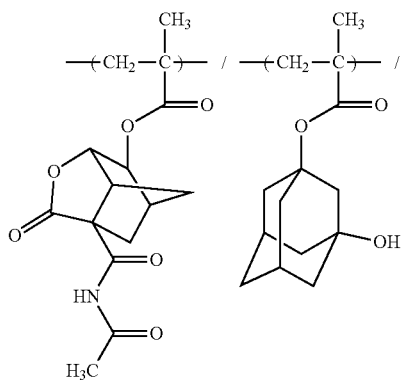

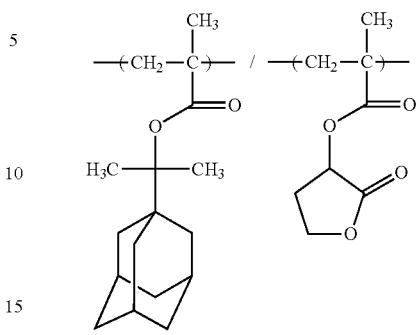

The procedure of Example 3 was performed, except for using, as monomer components, 10.58 g (34.5 mmol) of 1-(N-acetylcarbamoyl)-5-methacryloyloxy-3-oxatricyclo[4.2.1.0$^{4,8}$]nonan-2-one, 5.42 g (23.0 mmol) of 1-hydroxy-3-methacryloyloxyadamantane, 12.04 g (46.0 mmol) of 1-(1-methacryloyloxy-1-methylethyl)adamantane, and 1.95 g (11.5 mmol) of α-methacryloyloxy-γ-butyrolactone, and yielded 27.1 g of the desired polymeric compound. The polymeric compound as recovered was analyzed by GPC and found to have a weight-average molecular weight (Mw) of 8400 and a molecular weight distribution (Mw/Mn) of 1.84.

Example 9

Synthesis of Polymeric Compound (Copolymer) Having Structure:

[Chem. 27]

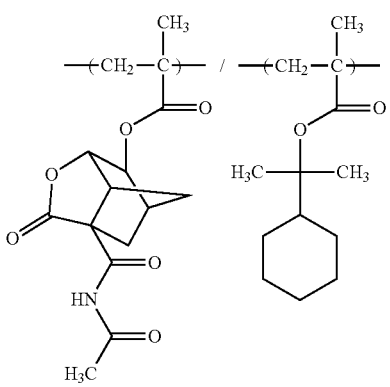

The procedure of Example 3 was performed, except for using, as monomer components, 14.81 g (48.2 mmol) of 1-(N-acetylcarbamoyl)-5-methacryloyloxy-3-oxatricyclo[4.2.1.0$^{4,8}$]nonan-2-one and 15.19 g (72.3 mmol) of 1-(1-methacryloyloxy-1-methylethyl)cyclohexane, and yielded 24.2 g of the desired polymeric compound. The polymeric compound as recovered was analyzed by GPC and found to have a weight-average molecular weight (Mw) of 8600 and a molecular weight distribution (Mw/Mn) of 1.88.

Example 10

Synthesis of Polymeric Compound (Copolymer) Having Structure:

[Chem. 28]

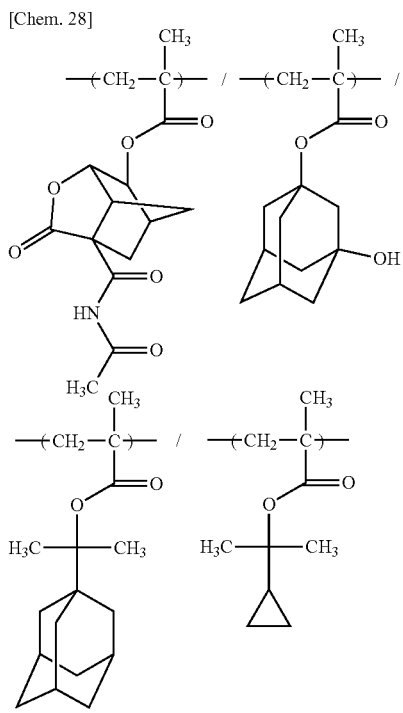

The procedure of Example 3 was performed, except for using, as monomer components, 13.88 g (45.2 mmol) of 1-(N-acetylcarbamoyl)-5-methacryloyloxy-3-oxatricyclo[4.2.1.0$^{4,8}$]nonan-2-one, 5.34 g (22.6 mmol) of 1-hydroxy-3-methacryloyloxyadamantane, 8.88 g (33.9 mmol) of 1-(1-methacryloyloxy-1-methylethyl)adamantane, and 1.90 g (11.3 mmol) of 1-(1-methacryloyloxy-1-methylethyl)cyclopropane, and yielded 27.2 g of the desired polymeric compound. The polymeric compound as recovered was analyzed by GPC and found to have a weight-average molecular weight (Mw) of 8800 and a molecular weight distribution (Mw/Mn) of 1.89.

Example 11

Synthesis of Polymeric Compound (Copolymer) Having Structure:

[Chem. 29]

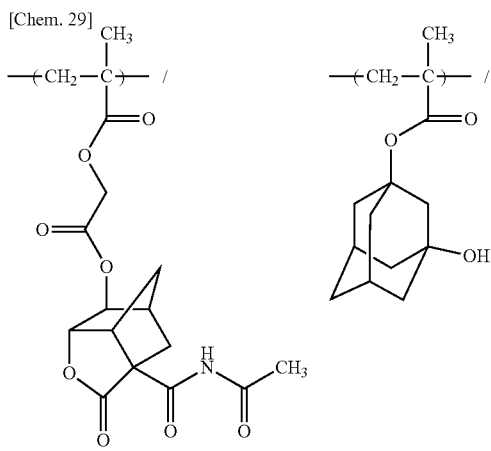

-continued

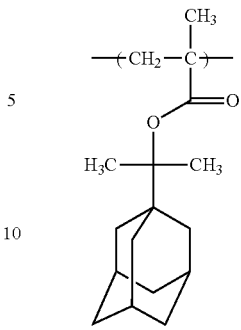

The procedure of Example 3 was performed, except for using, as monomer components, 14.70 g (40.3 mmol) of 1-(N-acetylcarbamoyl)-5-(2-methacryloyloxyacetoxy)-3-oxatricyclo[4.2.1.0$^{4,8}$]nonan-2-one, 4.75 g (20.1 mmol) of 1-hydroxy-3-methacryloyloxyadamantane, and 10.55 g (40.3 mmol) of 1-(1-methacryloyloxy-1-methylethyl)adamantane, and yielded 27.4 g of the desired polymeric compound. The polymeric compound as recovered was analyzed by GPC and found to have a weight-average molecular weight (Mw) of 8300 and a molecular weight distribution (Mw/Mn) of 1.83.

Comparative Example 1

Synthesis of Polymeric Compound (Copolymer) Having Structure:

[Chem. 30]

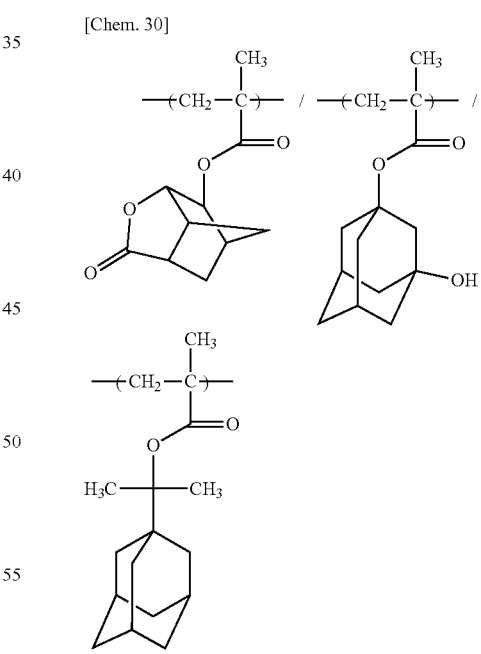

The procedure of Example 3 was performed, except for using, as monomer components, 11.06 g (49.8 mmol) of 5-methacryloyloxy-3-oxatricyclo[4.2.1.0$^{4,8}$]nonan-2-one, 5.88 g (24.9 mmol) of 1-hydroxy-3-methacryloyloxyadamantane, and 13.06 g (49.8 mmol) of 1-(1-methacryloyloxy-1-methylethyl)adamantane, and yielded 28.0 g of the desired polymeric compound. The polymeric compound as recovered was analyzed by GPC and found to have a weight-average molecular weight (Mw) of 8500 and a molecular weight distribution (Mw/Mn) of 1.86.

Comparative Example 2

Synthesis of Polymeric Compound (Copolymer) Having Structure:

[Chem. 31]

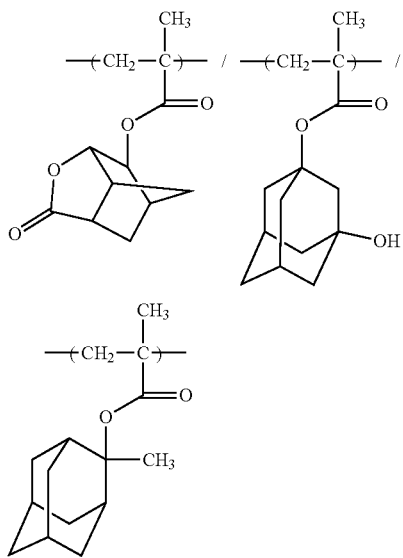

The procedure of Example 3 was performed, except for using, as monomer components, 11.60 g (52.3 mmol) of 5-methacryloyloxy-3-oxatricyclo[4.2.1.0$^{4,8}$]nonan-2-one, 6.17 g (26.1 mmol) of 1-hydroxy-3-methacryloyloxyadamantane, and 12.23 g (52.3 mmol) of 2-methacryloyloxy-2-methyladamantane, and yielded 25.9 g of the desired polymeric compound. The polymeric compound as recovered was analyzed by GPC and found to have a weight-average molecular weight (Mw) of 9000 and a molecular weight distribution (Mw/Mn) of 1.90.

Comparative Example 3

Synthesis of Polymeric Compound (Copolymer) Having Structure:

[Chem. 32]

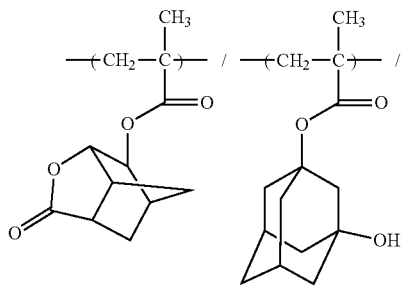

-continued

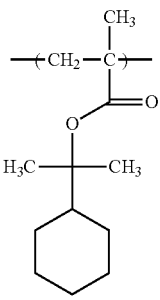

The procedure of Example 3 was performed, except for using, as monomer components, 12.11 g (54.5 mmol) of 5-methacryloyloxy-3-oxatricyclo[4.2.1.0$^{4,8}$]nonan-2-one, 6.44 g (27.3 mmol) of 1-hydroxy-3-methacryloyloxyadamantane, and 11.45 g (54.5 mmol) of 2-methacryloyloxy-2-methyladamantane, and yielded 28.1 g of the desired polymeric compound. The polymeric compound as recovered was analyzed by GPC and found to have a weight-average molecular weight (Mw) of 8700 and a molecular weight distribution (Mw/Mn) of 1.87.

Comparative Example 4

Synthesis of Polymeric Compound (Copolymer) Having Structure:

[Chem. 33]

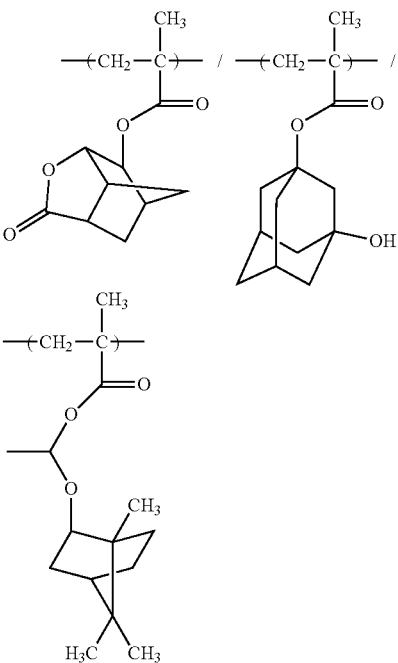

The procedure of Example 3 was performed, except for using, as monomer components, 10.99 g (49.5 mmol) of 5-methacryloyloxy-3-oxatricyclo[4.2.1.0$^{4,8}$]nonan-2-one, 5.84 g (24.8 mmol) of 1-hydroxy-3-methacryloyloxyadamantane, and 13.70 g (49.5 mmol) of 1-(bornyloxy)ethyl methacrylate, and yielded 26.9 g of the desired polymeric compound. The polymeric compound as recovered was analyzed by GPC and found to have a weight-average molecular weight (Mw) of 8500 and a molecular weight distribution (Mw/Mn) of 1.85.

Comparative Example 5

Synthesis of Polymeric Compound (Copolymer) Having Structure:

[Chem. 34]

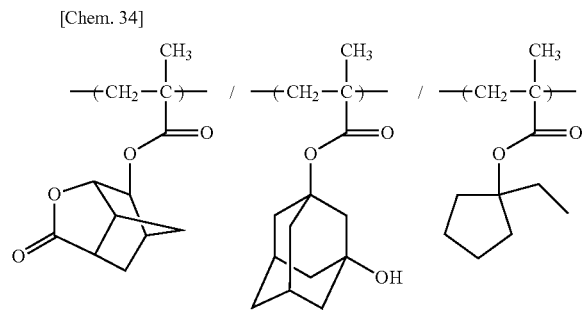

The procedure of Example 3 was performed, except for using, as monomer components, 12.76 g (57.5 mmol) of 5-methacryloyloxy-3-oxatricyclo[4.2.1.0$^{4,8}$]nonan-2-one, 6.78 g (28.7 mmol) of 1-hydroxy-3-methacryloyloxyadamantane, and 10.46 g (57.5 mmol) of 1-methacryloyloxy-1-ethylcyclopentane, and yielded 26.7 g of the desired polymeric compound. The polymeric compound as recovered was analyzed by GPC and found to have a weight-average molecular weight (Mw) of 9100 and a molecular weight distribution (Mw/Mn) of 1.90.

Comparative Example 6

Synthesis of Polymeric Compound (Copolymer) Having Structure:

[Chem. 35]

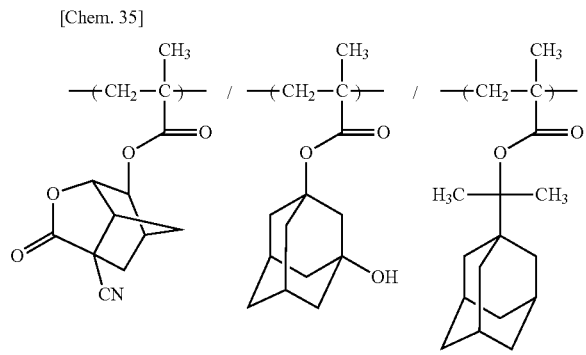

The procedure of Example 3 was performed, except for using, as monomer components, 11.82 g (47.8 mmol) of 1-cyano-5-methacryloyloxy-3-oxatricyclo[4.2.1.0$^{4,8}$]nonan-2-one, 5.65 g (23.9 mmol) of 1-hydroxy-3-methacryloyloxyadamantane, and 12.54 g (47.8 mmol) of 1-(1-methacryloyloxy-1-methylethyl)adamantane, and yielded 28.2 g of the desired polymeric compound. The polymeric compound as recovered was analyzed by GPC and found to have a weight-average molecular weight (Mw) of 8400 and a molecular weight distribution (Mw/Mn) of 1.85.

Evaluation Test

The polymers (polymeric compounds; resins) for photoresist use prepared in the examples and comparative examples were each combined with, and dissolved in propylene glycol monomethyl ether acetate (PGMEA) to give PGMEA solutions each having a polymer concentration of 20 percent by weight. The resulting photoresist-use polymer solutions were each combined with 10 parts by weight of triphenylsulfonium hexafluoroantimonate per 100 parts by weight of the polymer, further combined with PGMEA to be adjusted to have a polymer concentration of 15 percent by weight, filtrated through a filter having a pore size of 0.02 µm, and yielded photoresist compositions.

The photoresist compositions were each applied to a silicon wafer by spin coating to form a photosensitive layer having a thickness of 0.7 µm. The resulting articles were pre-baked on a hot plate at a temperature of 100° C. for 150 seconds, exposed to light from ArF excimer laser at a wavelength of 193 nm through a mask at an irradiance of 30 mJ/cm$^2$, and post-baked at a temperature of 100° C. for 60 seconds. Next, the articles were subjected to development with a 2.38 M aqueous tetramethylammonium hydroxide solution for 60 seconds and rinsed with ultrapure water. The photoresist-use polymer solutions prepared in the examples and comparative examples each gave a 0.25-µm line-and-space pattern, but those prepared in the examples gave obviously more clear patterns with less defects as compared with the polymer solutions prepared in the comparative examples.

The invention claimed is:

1. A monomer comprising an N-acylcarbamoyl group and a lactone skeleton, the monomer being represented by Formula (1):

[Chem. 1]

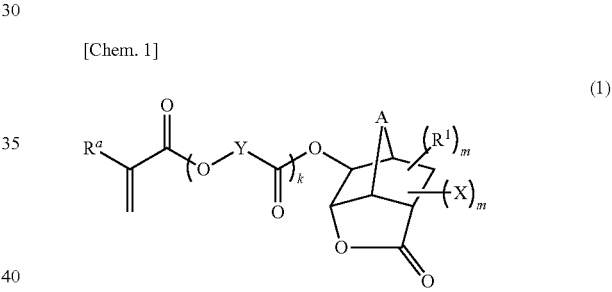

(1)

wherein:
$R^a$ is selected from hydrogen, halogen, and optionally substituted $C_1$-$C_6$ alkyl;
$R^1$ is a substituent bonded to ring and is, independently in each occurrence, selected from halogen, optionally halogenated $C_1$-$C_6$ alkyl, optionally halogenated and optionally hydroxy-protected $C_1$-$C_6$ hydroxyalkyl, carboxy which may form a salt, and substituted oxycarbonyl;
"A" is selected from $C_1$-$C_6$ alkylene, oxygen, sulfur, and non-bond;
m is a number of occurrence of $R^1$ and represents an integer of 0 to 8;
X represents, independently in each occurrence, N-acylcarbamoyl represented by Formula (2):

[Chem. 2]

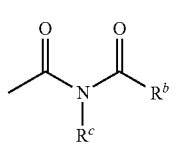

(2)

where $R^b$ and $R^c$ are each independently selected from hydrogen and an optionally substituted non-aromatic hydrocarbon group, where $R^b$ and $R^c$ may be linked to each other to form a ring with specified nitrogen atom and carbon atom;

n is a number of occurrence of X bonded to ring and represents an integer of 1 to 9;

Y represents a $C_1$-$C_6$ divalent organic group; and k is selected from 0 and 1, where $CH_2=C(R^a)CO-(O-Y-CO)_k-O-$ group may have either of an endo conformation and an exo conformation.

2. The monomer comprising an N-acylcarbamoyl group and a lactone skeleton according to claim 1, wherein the monomer comprises a compound represented by Formula (1a):

[Chem. 3]

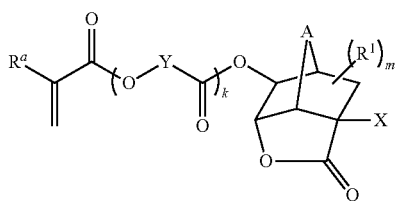

(1a)

wherein:
$R^a$ is selected from hydrogen, halogen, and optionally substituted $C_1$-$C_6$ alkyl;

$R^1$ is a substituent bonded to ring and is, independently in each occurrence, selected from halogen, optionally halogenated $C_1$-$C_6$ alkyl, optionally halogenated and optionally hydroxy-protected $C_1$-$C_6$ hydroxyalkyl, carboxy which may form a salt, and substituted oxycarbonyl;

"A" is selected from $C_1$-$C_6$ alkylene, oxygen, sulfur, and non-bond;

m is a number of occurrence of $R^1$ and represents an integer of 0 to 8;

X represents N-acylcarbamoyl represented by Formula (2):

[Chem. 4]

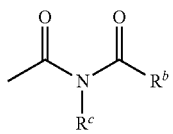

(2)

where $R^b$ and $R^c$ are each independently selected from hydrogen and an optionally substituted non-aromatic hydrocarbon group, where $R^b$ and $R^c$ may be linked to each other to form a ring with specified nitrogen atom and carbon atom;

Y represents a $C_1$-$C_6$ divalent organic group; and k is selected from 0 and 1, where $CH_2=C(R^a)CO-(O-Y-CO)_k-O-$ group may have either of an endo conformation and an exo conformation.

3. A polymeric compound comprising a monomer unit represented by Formula (I):

[Chem. 5]

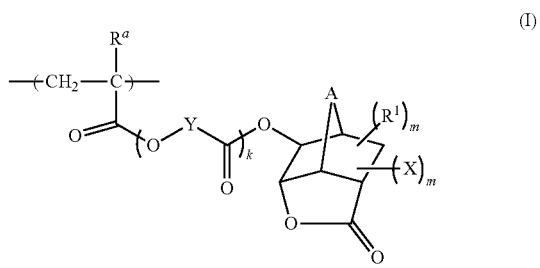

(I)

wherein:
$R^a$ is selected from hydrogen, halogen, and optionally substituted $C_1$-$C_6$ alkyl;

$R^1$ is a substituent bonded to ring and is, independently in each occurrence, selected from halogen, optionally halogenated $C_1$-$C_6$ alkyl, optionally halogenated and optionally hydroxy-protected $C_1$-$C_6$ hydroxyalkyl, carboxy which may form a salt, and substituted oxycarbonyl;

"A" is selected from $C_1$-$C_6$ alkylene, oxygen, sulfur, and non-bond;

m is a number of occurrence of $R^1$ and represents an integer of 0 to 8;

X represents, independently in each occurrence, N-acylcarbamoyl represented by Formula (2):

[Chem. 6]

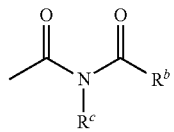

(2)

where $R^b$ and $R^c$ are each independently selected from hydrogen and an optionally substituted non-aromatic hydrocarbon group, where $R^b$ and $R^c$ may be linked to each other to form a ring with specified nitrogen atom and carbon atom;

n is a number of occurrence of X bonded to ring and represents an integer of 1 to 9;

Y represents a $C_1$-$C_6$ divalent organic group; and k is selected from 0 and 1, where $CH_2=C(R^a)CO-(O-Y-CO)_k-O-$ group may have either of an endo conformation and an exo conformation.

4. The polymeric compound according to claim 3, wherein the monomer unit represented by Formula (I) comprises a monomer unit represented by Formula (Ia):

[Chem. 7]

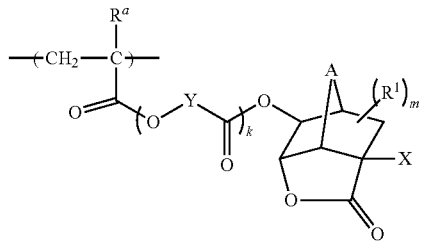

(Ia)

wherein:
- $R^a$ is selected from hydrogen, halogen, and optionally substituted $C_1$-$C_6$ alkyl;
- $R^1$ is a substituent bonded to ring and is, independently in each occurrence, selected from halogen, optionally halogenated $C_1$-$C_6$ alkyl, optionally halogenated and optionally hydroxy-protected $C_1$-$C_6$ hydroxyalkyl, carboxy which may form a salt, and substituted oxycarbonyl;
- "A" is selected from $C_1$-$C_6$ alkylene, oxygen, sulfur, and non-bond;
- m is a number of occurrence of $R^1$ and represents an integer of 0 to 8;
- X represents N-acylcarbamoyl represented by Formula (2):

[Chem. 8]

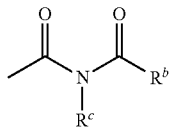
(2)

where $R^b$ and $R^c$ are each independently selected from hydrogen and an optionally substituted non-aromatic hydrocarbon group, where $R^b$ and $R^c$ may be linked to each other to form a ring with specified nitrogen atom and carbon atom;
- Y represents a $C_1$-$C_6$ divalent organic group; and
- k is selected from 0 and 1,
  where $CH_2$=$C(R^a)CO$—$(O$—$Y$—$CO)_k$—$O$— group may have either of an endo conformation and an exo conformation.

5. The polymeric compound according to claim 3, further comprising
   a monomer unit capable of releasing a moiety thereof by the action of an acid to develop alkali solubility.

6. The polymeric compound according to claim 5,
   wherein the monomer unit capable of releasing a moiety thereof by the action of an acid to develop alkali solubility comprises at least one monomer unit selected from the group consisting of monomer units represented by Formulae (Va) to (Vd):

[Chem. 9]

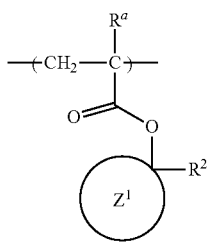
(Va)

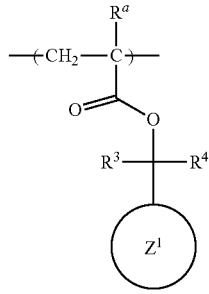
(Vb)

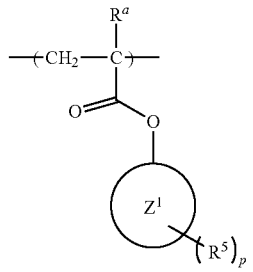
(Vc)

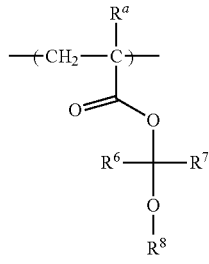
(Vd)

wherein:
- Ring $Z^1$ represents an optionally substituted $C_3$-$C_{20}$ alicyclic hydrocarbon ring;
- $R^a$ is, independently in each occurrence, selected from hydrogen, halogen, and optionally substituted $C_1$-$C_6$ alkyl;
- $R^2$, $R^3$, and $R^4$ represent, identically or differently, optionally substituted $C_1$-$C_6$ alkyl;
- $R^5$ is a substituent bonded to Ring $Z^1$ and is, independently in each occurrence, selected from oxo, alkyl, optionally protected hydroxy, optionally protected hydroxyalkyl, and optionally protected carboxy, where at least one of occurrence(s) of $R^5$ in a number of p represents a —$COOR^d$ group, where $R^d$ is selected from an optionally substituted tertiary hydrocarbon group, tetrahydrofuranyl, tetrahydropyranyl, and oxepanyl;
- p represents an integer of 1 to 3;
- $R^6$ and $R^7$ are, identically or differently, selected from hydrogen and optionally substituted $C_1$-$C_6$ alkyl; and
- $R^8$ is selected from hydrogen and an organic group,
where at least two of $R^6$, $R^7$, and $R^8$ may be linked to each other to form a ring with adjacent atom or atoms.

7. The polymeric compound according to claim 3, further comprising
   a monomer unit comprising an alicyclic skeleton substituted with at least one substituent.

8. The polymeric compound according to claim 7,
   wherein the monomer unit comprising an alicyclic skeleton substituted with at least one substituent comprises at least one monomer unit selected from monomer units represented by Formula (VI):

[Chem. 10]

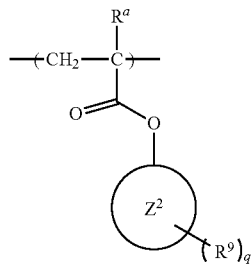

(VI)

wherein:
Ring $Z^2$ represents a $C_6$-$C_{20}$ alicyclic hydrocarbon ring;
$R^a$ is selected from hydrogen, halogen, and optionally substituted $C_1$-$C_6$ alkyl;
$R^9$ is a substituent bonded to Ring $Z^2$ and is, independently in each occurrence, selected from oxo, alkyl, haloalkyl, halogen, optionally protected hydroxy, optionally protected hydroxyalkyl, optionally protected mercapto, optionally protected carboxy, optionally protected amino, and optionally protected sulfo; and
q is a number of occurrence(s) of $R^9$ and represents an integer of 1 to 5.

9. The polymeric compound according to claim 5,
wherein the polymeric compound comprises:
the monomer unit represented by Formula (I);
the monomer unit capable of releasing a moiety thereof by the action of an acid to develop alkali solubility; and
a monomer unit comprising an alicyclic skeleton substituted with at least one substituent selected from hydroxy and hydroxymethyl.

10. The polymeric compound according to claim 3, further comprising
a monomer unit comprising a lactone skeleton and excluding the monomer unit represented by Formula (I).

11. The polymeric compound according to claim 4, further comprising
a monomer unit capable of releasing a moiety thereof by the action of an acid to develop alkali solubility.

12. The polymeric compound according to claim 4, further comprising
a monomer unit comprising an alicyclic skeleton substituted with at least one substituent.

13. The polymeric compound according to claim 5, further comprising
a monomer unit comprising an alicyclic skeleton substituted with at least one substituent.

14. The polymeric compound according to claim 6, further comprising
a monomer unit comprising an alicyclic skeleton substituted with at least one substituent.

15. The polymeric compound according to claim 6,
wherein the polymeric compound comprises:
the monomer unit represented by Formula (I);
the monomer unit capable of releasing a moiety thereof by the action of an acid to develop alkali solubility; and
a monomer unit comprising an alicyclic skeleton substituted with at least one substituent selected from hydroxy and hydroxymethyl.

16. The polymeric compound according to claim 4, further comprising
a monomer unit comprising a lactone skeleton and excluding the monomer unit represented by Formula (I).

17. The polymeric compound according to claim 5, further comprising
a monomer unit comprising a lactone skeleton and excluding the monomer unit represented by Formula (I).

18. The polymeric compound according to claim 6, further comprising
a monomer unit comprising a lactone skeleton and excluding the monomer unit represented by Formula (I).

19. The polymeric compound according to claim 7, further comprising
a monomer unit comprising a lactone skeleton and excluding the monomer unit represented by Formula (I).

20. The polymeric compound according to claim 8, further comprising
a monomer unit comprising a lactone skeleton and excluding the monomer unit represented by Formula (I).

* * * * *